(12) United States Patent
Ohrui et al.

(10) Patent No.: US 8,173,275 B2
(45) Date of Patent: May 8, 2012

(54) AZAINDENOCHRYSENE DERIVATIVE AND ORGANIC LIGHT-EMITTING DEVICE

(75) Inventors: Hiroki Ohrui, Kawasaki (JP); Masanori Muratsubaki, Hachioji (JP); Takeshi Sekiguchi, Tokyo (JP); Akihito Saitoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 394 days.

(21) Appl. No.: 12/613,460

(22) Filed: Nov. 5, 2009

(65) Prior Publication Data
US 2010/0117526 A1 May 13, 2010

(30) Foreign Application Priority Data
Nov. 7, 2008 (JP) .................. 2008-286726

(51) Int. Cl.
*H01L 51/54* (2006.01)

(52) U.S. Cl. ........ 428/690; 428/917; 313/504; 313/505; 313/506; 257/40; 257/E51.026; 257/E51.052; 544/234; 546/79; 546/81; 546/101

(58) Field of Classification Search .................. 428/690, 428/917; 313/504, 505, 506; 257/40, E51.026, 257/E51.052; 544/234; 546/79, 81, 101
See application file for complete search history.

(56) References Cited

U.S. PATENT DOCUMENTS
2004/0076853 A1* 4/2004 Jarikov .................. 428/690

FOREIGN PATENT DOCUMENTS
JP 2000-311786 A 11/2000

OTHER PUBLICATIONS

Joseph E. Rice Zhen-Wei Cai, "A Palladium-Catalyzed Intramolecular Arene-Triflate Coupling for the synthesis of Fluoranthenes and Benzofluoranthenes", Tetrahedron Letters 1992, vol. 33, No. 13, pp. 1675-1678.

* cited by examiner

*Primary Examiner* — Jennifer Chriss
*Assistant Examiner* — Gregory Clark
(74) *Attorney, Agent, or Firm* — Canon U.S.A., Inc., IP Division

(57) ABSTRACT

The invention provides an azaindenochrysene derivative, and an organic light-emitting device outputting light having high luminance and a long lifetime with high efficiency having an organic compound layer that includes the azaindenochrysene derivative.

9 Claims, 2 Drawing Sheets

AZAINDENOCHRYSENE DERIVATIVE AND ORGANIC LIGHT-EMITTING DEVICE

BACKGROUND OF THE INVENTION

1. Field of the Invention

The present invention relates to a novel organic compound having an azaindenochrysene skeleton and an organic light-emitting device having this novel organic compound as an organic light-emitting device material.

2. Description of the Related Art

An organic light emitting device is a device which includes a thin film which contains a fluorescent or phosphorescent organic compound and is interposed between electrodes, in which an exciton of the fluorescent or phosphorescent compound is generated when a hole and an electron are injected from the respective electrodes and which makes use of light radiated upon return of the exciton to its ground state. The recent progress of an organic light emitting device is significant, and the device suggests its potential to use in a wide variety of applications because of the following reasons. The device shows a high luminance at a low applied voltage. In addition, the device has a variety of emission wavelengths. Furthermore, the device can be a thin, light-weight light emitting device with high-speed responsiveness.

However, at present, an optical output with additionally higher luminance, or additionally higher conversion efficiency has been needed. In addition, the organic light emitting device still has many problems in terms of durability. For example, the device changes over time owing to long-term use, and deteriorates owing to an atmospheric gas containing oxygen, or to humidity or the like. Further, assuming that the device is applied to a full-color display or the like, the device must emit blue light, green light, and red light each having good color purity, but the problems concerning the color purity have not been sufficiently solved yet.

Japanese Patent Laid-Open No. 2000-311786 describes using azanaphthofluoranthene derivative compound as a green light-emitting material. The skeleton of such a compound places a limitation on light-emitting materials with a wavelength longer than that of green light.

SUMMARY OF THE INVENTION

The present invention has been made with a view to solving such problems of the prior art as described above. An object of the present invention is to provide a novel material for an organic light emitting device showing a light emission hue with an extremely good purity and outputting light having high luminance and a long lifetime with high efficiency.

Accordingly, an aspect of the present invention provides an azaindenochrysene derivative represented by General Formula [1] below:

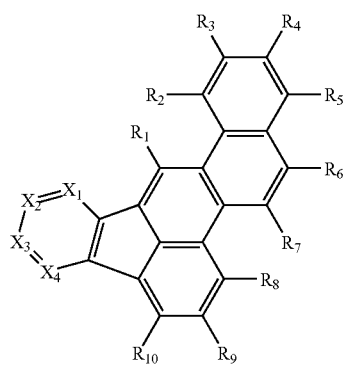

[1]

In General Formula [1], $X_1$ to $X_4$ each represent a carbon atom having a substituent R or a nitrogen atom, the carbon atom or the nitrogen atom forming a ring. R represents a hydrogen atom or a group selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. At least one of $X_1$ to $X_4$ represents a nitrogen atom. In a case where a plurality of carbon atoms having the substituent R are present, each R is independently identical to or different from each other.

$R_1$ to $R_{10}$ each represent a hydrogen atom, a halogen atom, or a group selected from at least one of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. $R_1$ to $R_{10}$ are independently identical to or different from each other.

Another aspect of the invention also provides the azaindenochrysene derivative represented by General Formula [2] below:

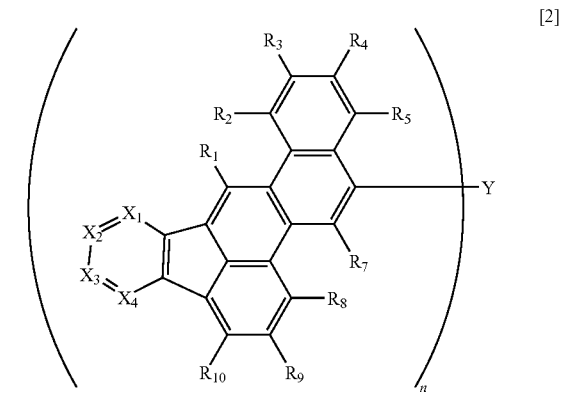

[2]

In General Formula [2], $X_1$ to $X_4$ each represent a carbon atom having a substituent R or a nitrogen atom, the carbon atom or the nitrogen atom forming a ring. R represents a hydrogen atom or is selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. At least one of $X_1$ to $X_4$ represents a nitrogen atom. In a case where a plurality of carbon atoms having the substituent R are present, each R is independently identical to or different from each other.

$R_1$ to $R_5$ and $R_7$ to $R_{10}$ each represent a hydrogen atom, a halogen atom, or a group selected from at least one of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. $R_1$ to $R_5$ and $R_7$ to $R_{10}$ are independently identical to or different from each other. Y represents at least one of a single bond and an n-valent linking group derived from at least one of a substituted or unsubstituted alkane, a substituted or unsubstituted alkene, a substituted or unsubstituted alkyne, a substituted or unsubstituted aromatic compound, a substituted or unsubstituted heterocyclic compound, a substituted or unsubstituted fused polycyclic aromatic compound, and a substituted or unsubstituted fused polycyclic heterocyclic compound; n represents an integer of equal to or greater than 2 and equal to or less than 4.

Another aspect of the invention also provides an organic light-emitting device having an anode, a cathode, and an organic compound layer disposed between the anode and the cathode, wherein the organic compound layer includes at least one compound represented by General Formula [1] or [2].

The invention can provide a novel azaindenochrysene derivative. In addition, an organic light emitting device containing a compound having an azaindenochrysene skeleton (azaindenochrysene derivative) can emit light having high luminance at a low applied voltage, and is excellent in durability.

In particular, a light-emitting device using the compound having an azaindenochrysene skeleton shows a blue light emission hue of very good purity with a light emission peak at a wavelength of 430 nm or greater and 460 nm or lower as a result of proper molecular modification. In addition, this organic light emitting device can emit light having high luminance at a low applied voltage, and is excellent in durability.

Further features of the present invention will become apparent from the following description of exemplary embodiments with reference to the attached drawings.

DETAILED DESCRIPTION OF THE EMBODIMENTS

Figure 1:
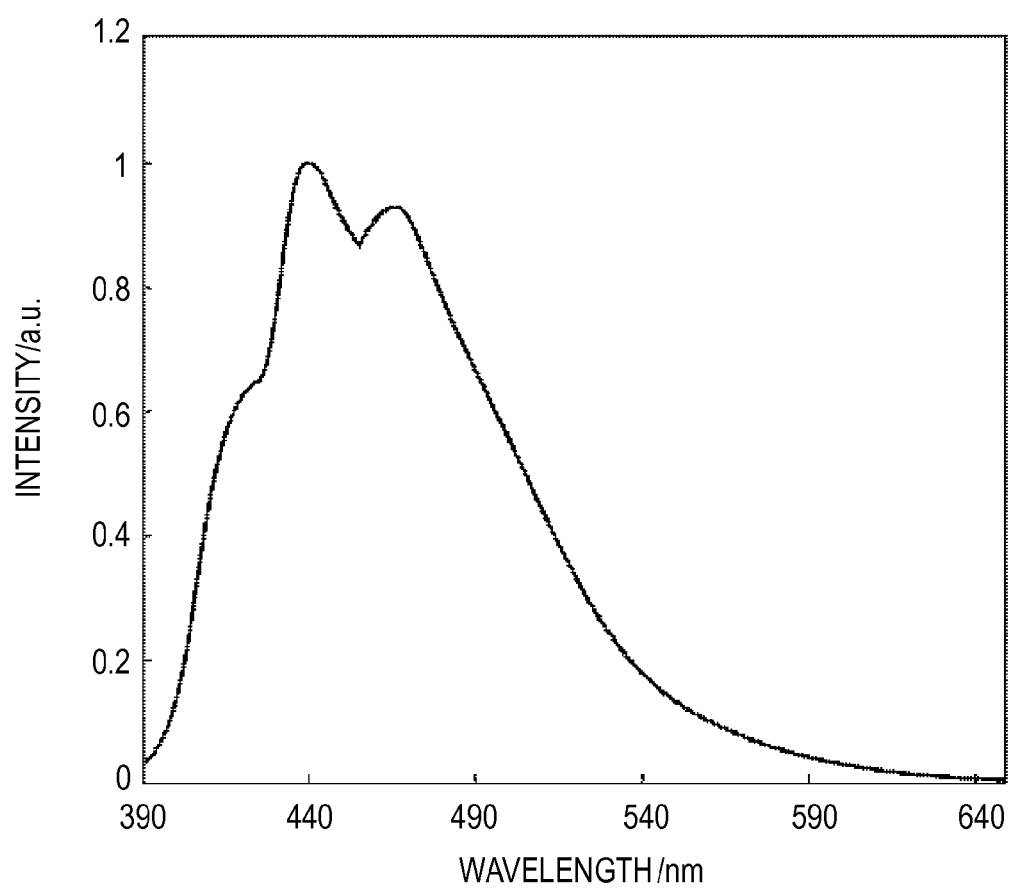
FIG. 1 shows a PL spectrum of a toluene solution ($1.0 \times 10^{-5}$ mol/L) of the intermediate compound 1.

The invention will be described below in detail.

First, an azaindenochrysene derivative according to an embodiment of the present invention will be described.

The azaindenochrysene derivative according to an embodiment of the present invention is represented by General Formula [1] below:

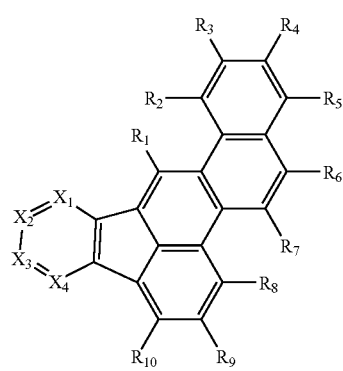

[1]

where $X_1$ to $X_4$ in General Formula [1] represent a carbon atom having a substituent R or a nitrogen atom, the carbon atom or the nitrogen atom forming a ring, and at least one of $X_1$ to $X_4$ is a nitrogen atom. R represents any of the following: a hydrogen atom or a group selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. In a case where a plurality of carbon atoms having a substituent R are present, each R may be independently identical to or different from each other.

In addition, $R_1$ to $R_{10}$ in General Formula [1] each represents any of the following: a hydrogen atom, a halogen atom, or a group selected from at least one of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. $R_1$ to $R_{10}$ may be independently identical to or different from each other.

$R_6$ in General Formula [1] may be selected from at least one of a substituted or unsubstituted aryl group, a substituted or unsubstituted fused polycyclic aromatic group, and a substituted or unsubstituted fused polycyclic heterocyclic group. Also, in one embodiment, both $X_1$ and $X_4$ may be nitrogen atoms.

The compound represented by General Formula [2] below is another compound according to an embodiment of the invention:

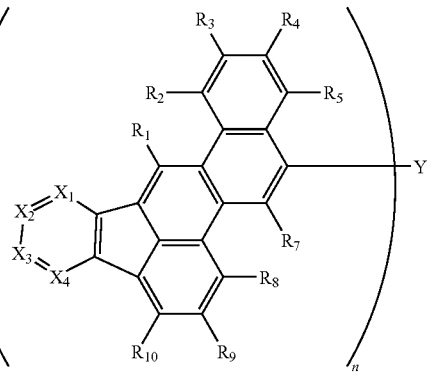

[2]

where General Formula [2], $X_1$ to $X_4$ each represent a carbon atom having a substituent R or a nitrogen atom, the carbon atom or the nitrogen atom forming a ring. R represents a hydrogen atom or a group selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. At least one of $X_1$ to $X_4$ may represent a nitrogen atom. In case where a plurality of carbon atoms having a substituent R are present, each R may be independently identical to or different from each other. $R_1$ to $R_5$ and $R_7$ to $R_{10}$ each represent a hydrogen atom, a halogen atom, or a group selected from the group consisting of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group. $R_1$ to $R_5$ and $R_7$ to $R_{10}$ may be independently identical to or different from each other. Y represents at least one of a single bond and an n-valent linking group derived from at least one of a substituted or unsubstituted alkane, a substituted or unsubstituted alkene, a substituted or unsubstituted alkyne, a substituted or unsubstituted aromatic compound, a substituted or unsubstituted heterocyclic compound, a substituted or unsubstituted fused polycyclic aromatic compound, and a substituted or unsubstituted fused polycyclic heterocyclic compound; n represents an integer of equal to or greater than 2 and equal to or less than 4. In one embodiment, the azaindenochrysene derivative according to General Formula [2] has $X_1$ and $X_4$ as nitrogen atoms.

The azaindenochrysene derivative according to embodiments of the invention can be used as a material for an organic light-emitting device. In a case where the compound is used for a light emitting layer in the device, the compound can be used alone in the light emitting layer, or can be used in the layer for the purpose of serving as a dopant (guest) material or a host material, whereby a device emitting light with high efficiency, maintaining high luminance for a long time period, and showing small deterioration due to energization can be obtained.

The azaindenochrysene derivative represented by General Formula [1] or [2] of the invention may be used as a guest in a light-emitting layer having a host and a guest.

The azaindenochrysene derivative represented by General Formula [1] or [2] of the invention can be used as a material for an organic light-emitting device, and it can be used not only in the light-emitting layer, but also, for example, as an electron transport layer or electron injection layer.

In a case where the light-emitting layer comprises a host material that has carrier transport property and a guest, the following several processes are involved in light emission.

1. the transport of an electron or a hole in the light emission layer;
2. the generation of an exciton of the host;
3. the transfer of excitation energy between host molecules; and
4. the transfer of excitation energy from the host to the guest.

The desired energy transfer or light emission in each process competes with various deactivation processes.

An improvement in luminous efficiency of an EL device involves a material that is itself mainly responsible for light emission to have a large light emission quantum yield. However, how efficiently energy can be transferred between hosts or between a host and a guest may also be of concern. In addition, no cause for the degradation of light emission due to energization has been revealed at present. However, the degradation is assumed to be related to at least the material itself that is mainly responsible for light emission or a change in environment surrounding the luminescent material due to a molecule around the material.

In view of the foregoing, the inventors of the present invention have made various studies, and have found that, when an azaindenochrysene derivative represented by the general formula [1] and [2] according to embodiments of the invention is especially used as a host or guest for the light emission layer of a device, the device emits light with high efficiency, maintains high luminance for a long time period, and shows small degradation of light emission due to energization.

It has already been mentioned that the azaindenochrysene derivative represented by General Formulas [1] and [2] may be used for the guest of the light-emitting layer, but the azaindenochrysene derivative may be also used as the host of the light-emitting layer.

Because the azaindenochrysene derivative of the invention has a relatively high glass transition temperature, so an achievement in high durability of an organic EL device can be expected. Thus, in a case where the azaindenochrysene derivative of the invention is produced as a film, crystallization can be prevented. This is because the azaindenochrysene derivative has a nitrogen-containing aromatic heterocyclic group. As a result, stable amorphous film properties are demonstrated.

Further, the azaindenochrysene derivative represented by General Formulas [1] and [2] according to embodiments of the invention may have an atom with a high electronegativity in a fused aromatic ring structure. As a result, it has a high a reduction potential and large electron accepting ability.

Therefore, from among the layers constituting the organic light-emitting device, the azaindenochrysene derivative represented by General Formulas [1] and [2] according to embodiments of the invention can be used not only in an organic compound layer comprising the light-emitting layer, but also in an electron transport layer or an electron injection layer. For example, the derivative may be used in the electron transport layer.

The electron mobility can be regulated by controlling the reduction potential by selecting R, $R_1$ to $R_{10}$, and Y in the azaindenochrysene derivative represented by General Formulas [1] and [2].

Thus, by adequately selecting R, $R_1$ to $R_{10}$, and Y in the azaindenochrysene derivative represented by General Formulas [1] and [2] by combining various host materials, it is possible to maintain high luminance for a long period at a low drive voltage and reduce degradation of light emission due to energization.

In addition, an improvement in quantum yield of a light emitting material to be used in an organic electroluminescence device may be indispensable for providing an organic electroluminescence device having an optical output with high efficiency. When a nitrogen atom is introduced mainly into a fused polycyclic aromatic group, the n-π* orbital of a triplet becomes an orbital at a Tn level (n represents 1 or more) depending on the position where the atom is introduced. Then, when the n-π* orbital (triplet) is energetically close to an S1 orbital, energy deactivation from the S1 orbital to the n-π* orbital is apt to occur, so the quantum yield of the light emitting material is apt to reduce. However, the proper selection of the position where the nitrogen atom is introduced and the kind of a substituent to be introduced into the molecular skeleton of the light emitting material can increase a difference in energy between the n-π* orbital (triplet) and the S1 orbital, and can alleviate the reduction in quantum yield. The position where the nitrogen atom is introduced is preferably simulated on the basis of molecular orbital calculation. That is, nitrogen atoms are more preferably introduced into the positions of $X_1$ and $X_2$ represented in the general formula [1] on the basis of the design of a molecular skeleton capable of maintaining high quantum yield.

Further, an emission spectrum having a controlled molecular vibration can be monodispersed, and its half width can be reduced by properly designing not only the position where a nitrogen atom is introduced but also the position and kind of a substituent to be introduced into the molecular skeleton of a light emitting material, so a light emitting material having a good color purity can be provided.

The present invention has been made as a result of molecular design based on the foregoing discussion.

Examples of the substituted or unsubstituted alkyl group that is represented by R and $R_1$ to $R_{10}$ in the General Formulas [1] and [2] are presented below, but this list is specifically not limiting.

A methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a fluoromethyl group, a difluoromethyl group, a trifluoromethyl group, a 2-fluoroethyl group, a 2,2,2-trifluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, a iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, an adamantyl group, a benzyl group, a 2-phenylethyl group, a 2-phenylisopropyl group, a 1-naphthylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of the alkenyl group represented by R and $R_1$ to $R_{10}$ include a vinyl group, a 1-propenyl group, a 2-propenyl group, a 1-butenyl group, a 2-butenyl group, and a 3-butenyl group, but this list is specifically not limiting.

Examples of the alkynyl group represented by R and $R_1$ to $R_{10}$ include an ethynyl group, a 1-propynyl group, a 2-propynyl group a 1-butynyl group, a 2-butynyl group, and a 3-butynyl group, but this list is specifically not limiting.

Examples of the substituted or unsubstituted aryl group represented by R and $R_1$ to $R_{10}$ include the groups listed below, but this list is specifically not limiting.

A phenyl group, a 4-methylphenyl group, a 4-ethylphenyl group, a 3,5-dimethylphenyl group, a 2,6-diethylphenyl group, a mesityl group, a 4-tert-butylphenyl group, a biphenyl group, and a 4-pyridylphenyl group.

Examples of the substituted or unsubstituted heterocyclic group represented by R and $R_1$ to $R_{10}$ include the groups listed below, but this list is specifically not limiting.

A pyridyl group, a pyrrolyl group, a bipyridyl group, a methylpyridyl group, a pyrimidinyl group, a pyradinyl group, a pyridazinyl group, a terpyrrolyl group, a thienyl group, a terphenyl group, a propylthienyl group, a furyloxazolyl group, an oxadiazolyl group, a thiazolyl group, and a thiadiazolyl group.

Examples of the substituted or unsubstituted fused polycyclic aromatic group represented by R and $R_1$ to $R_{10}$ include the groups listed below, but this list is specifically not limiting.

A naphthyl group, an acenapthylenyl group, an anthryl group, a phenanthryl group, a pyrenyl group, an acephenantolylenyl group, an aceanthrylenyl group, a chrysenyl group, a dibenzochrysenyl group, a benzoanthryl group, a dibenzoanthryl group, a naphthacenyl group, a picenyl group, a pentacenyl group, a fluorenyl group, a 9,9-dihydroanthryl group, a triphenylenyl group, a perylenyl group, a fluoranthenyl group, and a benzo[k]fluoranthenyl group.

Examples of the substituted or unsubstituted fused polycyclic heterocyclic group represented by R and $R_1$ to $R_{10}$ include the groups listed below, but this list is specifically not limiting.

A quinolyl group, an isoquinolyl group, a benzothienyl group, a dibenzothienyl group, a benzofuryl group, an isobenzofuryl group, a dibenzofuryl group, a quinoxalinyl group, a naphthylidinyl group, a quinazolinyl group, a phenanthridinyl group, an indolidinyl group, a phenazinyl group, a carbazolyl group, an acridinyl group, a phenazinyl group, a diazafluorenyl group, an azafluorenyl group, an azafluoranthenyl group, and an azabenzofluoranthenyl group.

Examples of a substituent which the above substituents may additionally have include those listed below, but this list is specifically not limiting.

An alkyl group such as a methyl group, an ethyl group, a propyl group, and a tert-butyl group, an aryl group such as a phenyl group and a biphenyl group, a heterocyclic group such as a thienyl group and a pyrrolyl group, a cyano group, and a nitro group.

In the General Formula [2], Y represents at least one of a single bond and an n-valent linking group derived from at least one of a substituted or unsubstituted alkane, a substituted or unsubstituted alkene, a substituted or unsubstituted alkyne, a substituted or unsubstituted aromatic compound, a substituted or unsubstituted heterocyclic compound, a substituted or unsubstituted fused polycyclic aromatic compound, and a substituted or unsubstituted fused polycyclic heterocyclic compound. In General Formula [2], n is an integer of equal to or greater than 2 and equal to or less than 4.

Examples of the linking group derived from the substituted or unsubstituted alkane represented by Y include an ethylene group, a propylene group, and a butylene group, but this list is specifically not limiting.

Examples of the linking group derived from the substituted or unsubstituted alkene represented by Y include a vinylene group, a propynylene group, and a butynylene group, but this list is specifically not limiting.

Examples of the linking group derived from the substituted or unsubstituted aromatic compound represented by Y include a phenylene group and a biphenylene group, but this list is specifically not limiting.

Examples of the linking group derived from the substituted or unsubstituted heterocyclic compound represented by Y include a pyridinylene group and a bipyridinylene group, but this list is specifically not limiting.

Examples of the linking group derived from the substituted or unsubstituted fused polycyclic aromatic cyclic compound represented by Y include a fluorenylene group, a bifluorenylene group, a naphthylene group, an anthrylene group, and a chrysenylene group, but this list is specifically not limiting.

Examples of the linking group derived from the substituted or unsubstituted fused polycyclic heterocyclic compound represented by Y include an azafluoronylene group, a diazafluorenylene group, and a naphthylidinylene group, but this list is specifically not limiting.

Examples of a substituent which the above substituents may additionally have include an alkyl group such as a methyl group, an ethyl group, a propyl group, and a tert-butyl group, an aryl group such as a phenyl group and a biphenyl group, a heterocyclic group such as a thienyl group and a pyrrolyl group, a cyano group, and a nitro group, but this list is specifically not limiting.

Hereinafter Specific structural formulas of the azaindenochrysene derivative of the present invention are shown below.

However, these are only representative examples, and the present invention is not limited thereto.

COMPOUND EXAMPLE 1

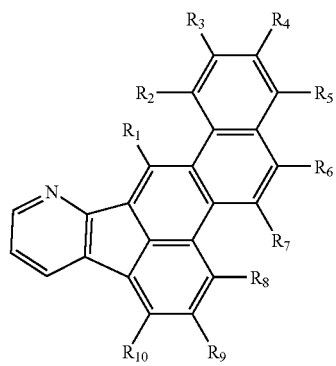
[3]

In this compound example, in General Formula [3] above, $R_6$: an aryl group such as a biphenyl group or a terphenyl group;

$R_1$ to $R_5$ and $R_7$ to $R_{10}$: a hydrogen atom or an alkyl group such as at least one of a methyl group and a tertiary butyl group, $R_1$ to $R_5$ and $R_7$ to $R_{10}$ may be identical to or different from each other.

101

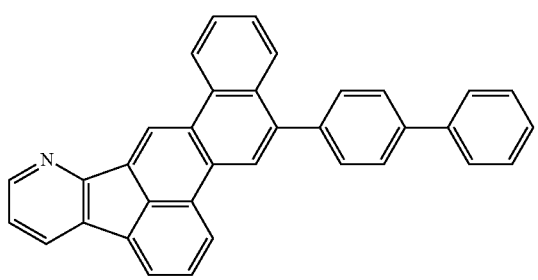

102

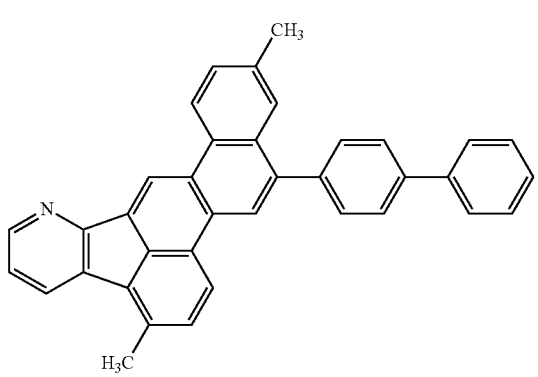

103

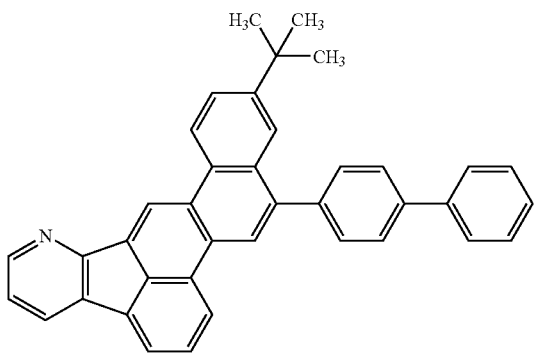

104

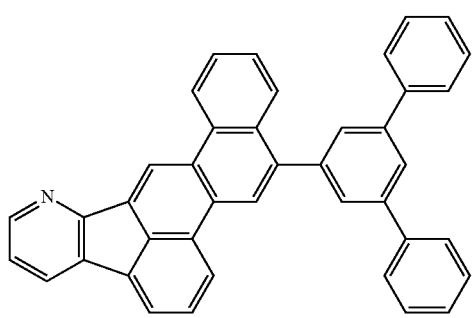

105

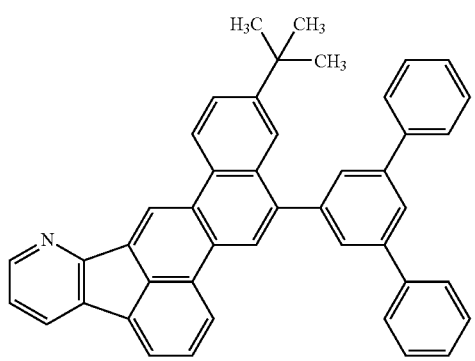

106

107

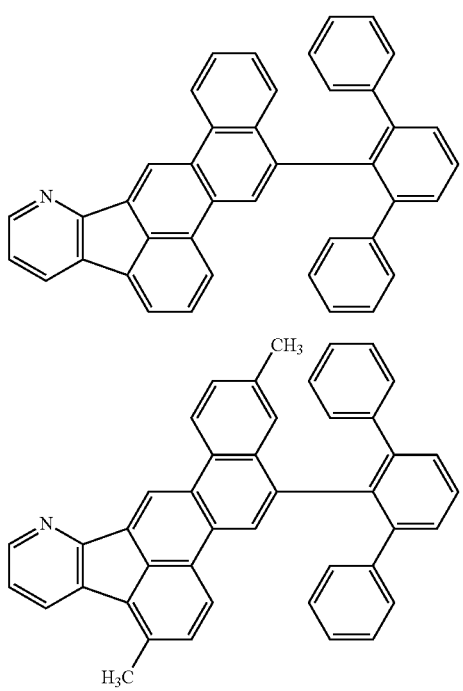

108

COMPOUND EXAMPLE 2

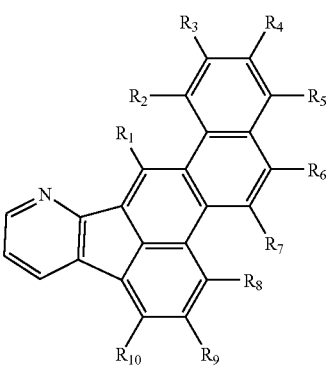

[3]

In this compound example, in General Formula [3] above, $R_6$: a fused polycyclic group with three or less rings, such as at least one of a naphthyl group and a fluorenyl group.

$R_1$ to $R_5$ and $R_7$ to $R_{10}$: a hydrogen atom, an alkyl group such as at least one of a methyl group and a tertiary butyl group, or an aryl group such as a phenyl group.

$R_1$ to $R_5$ and $R_7$ to $R_{10}$ may be identical to or different from each other.

201

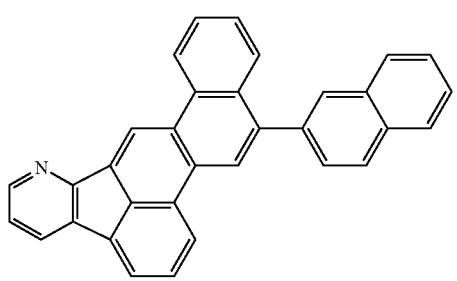

202

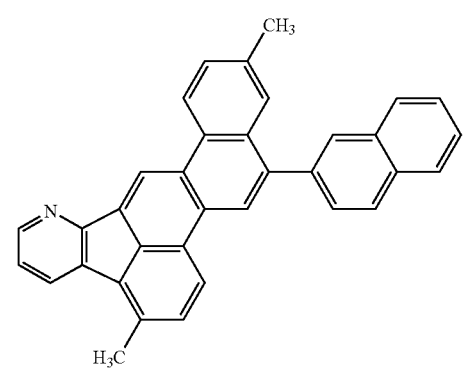

203

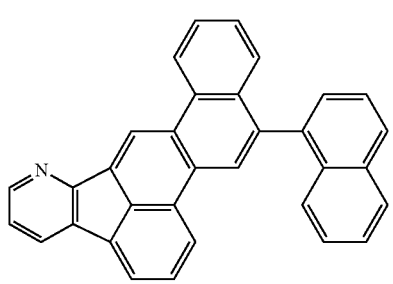

204

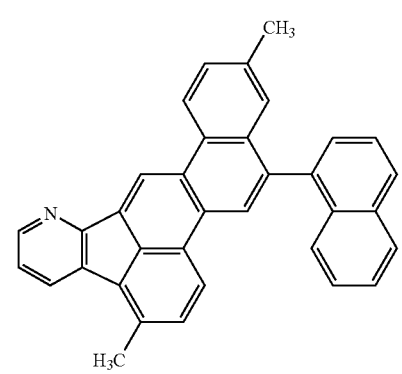

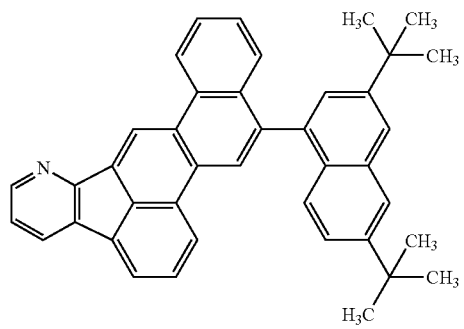

-continued
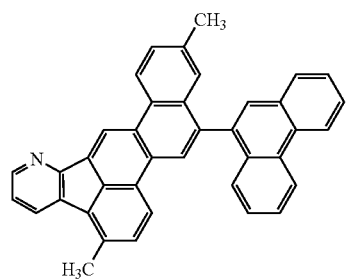 213
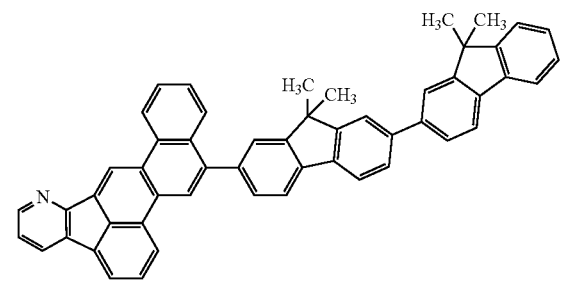 214
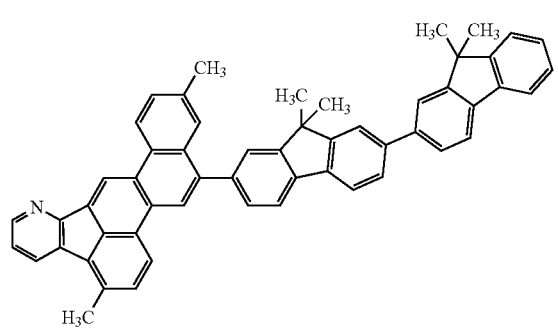 215
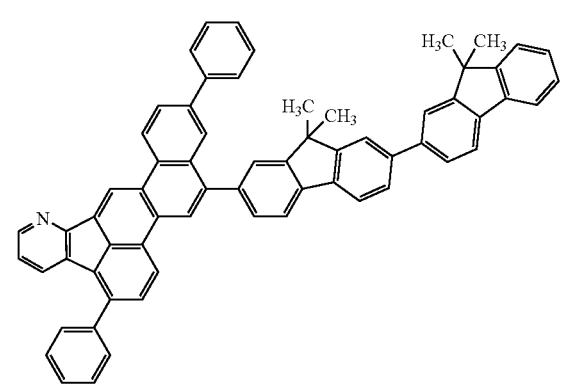 216
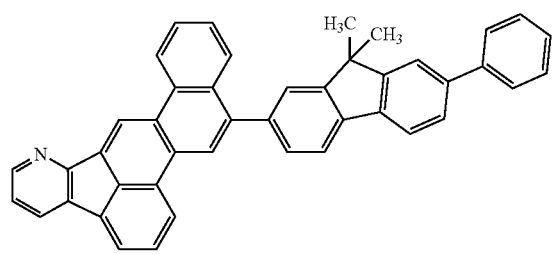 217
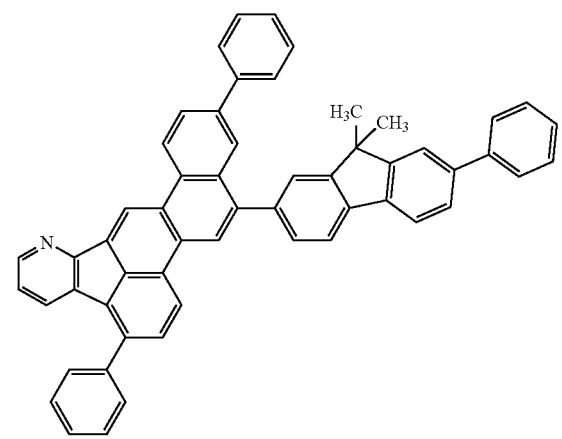 218
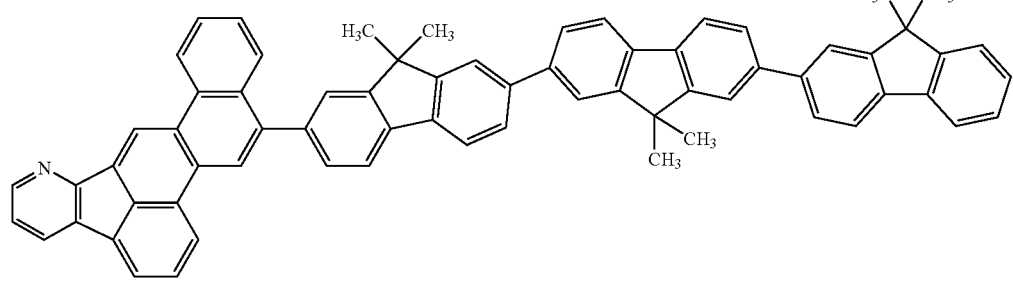 219

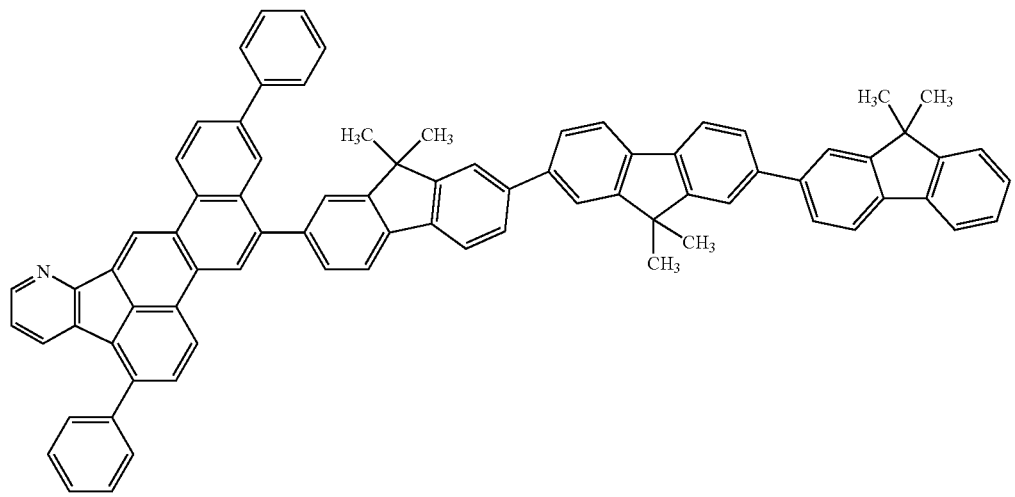

COMPOUND EXAMPLE 3

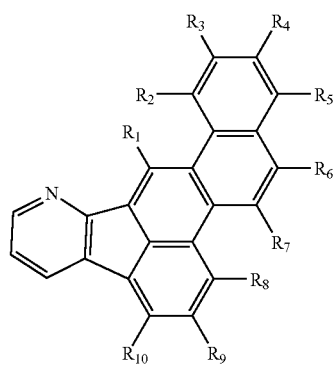

In this compound example, in General Formula [3] above, $R_6$: a fused polycyclic group with four or more and six or less rings, such as at least one of a fluoranthenyl group and benzofluoranthenyl group.

$R_1$ to $R_5$ and $R_7$ to $R_{10}$: a hydrogen atom, an alkyl group such as at least one of a methyl group and a tertiary butyl group, or an aryl group such as a phenyl group.

$R_1$ to $R_5$ and $R_7$ to $R_{10}$ may be identical to or different from each other.

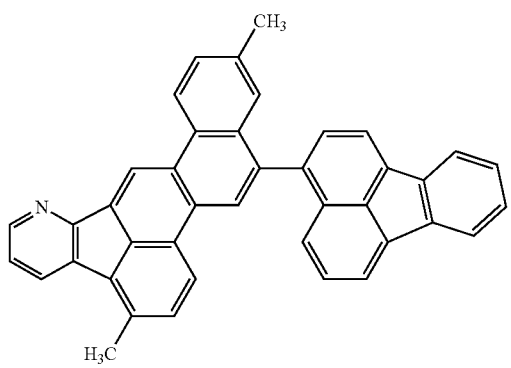

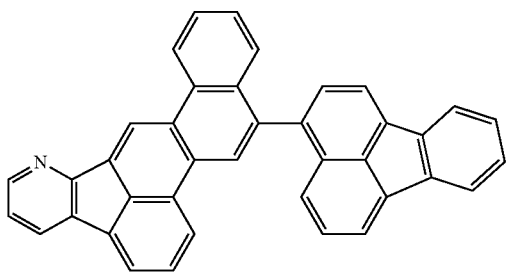

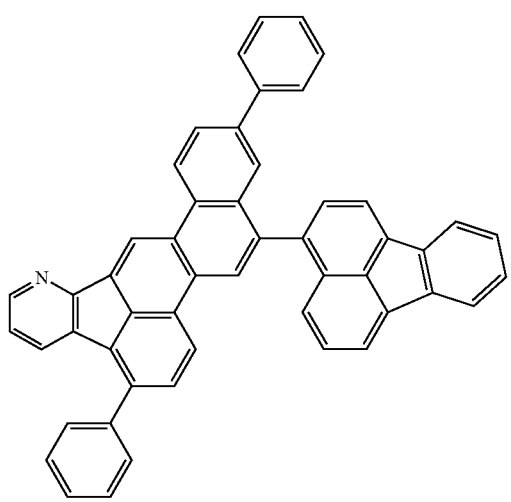

304
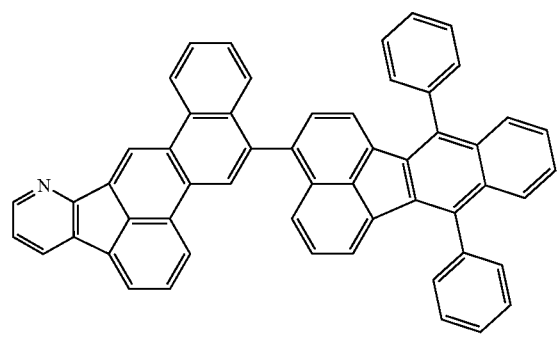
305
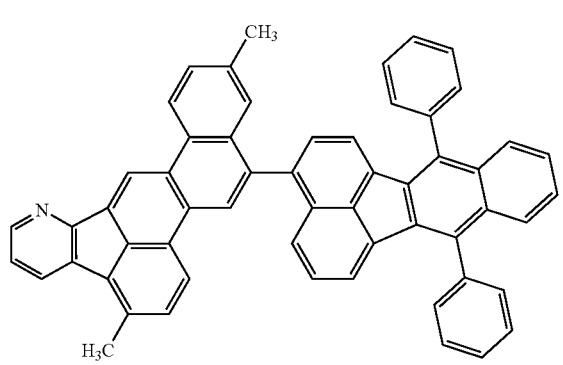
306
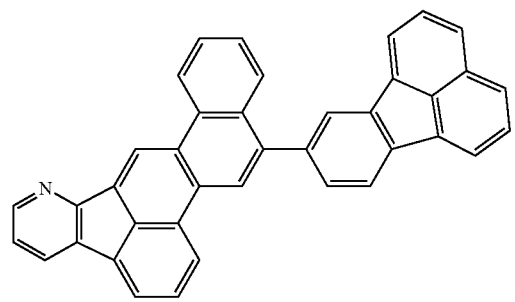
307
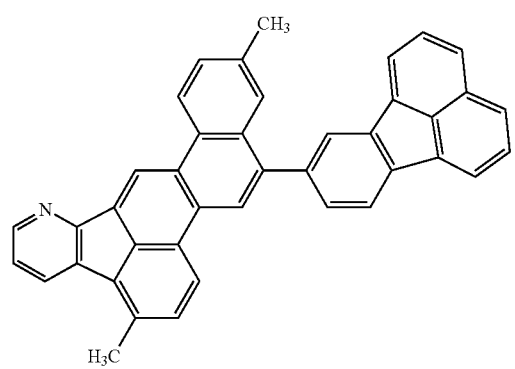
308
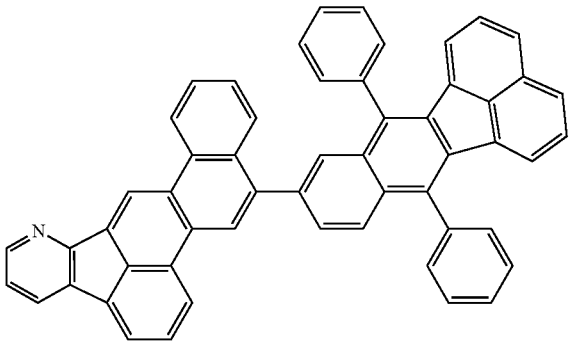
309
310
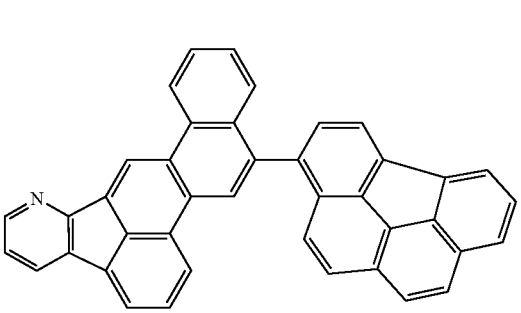
311
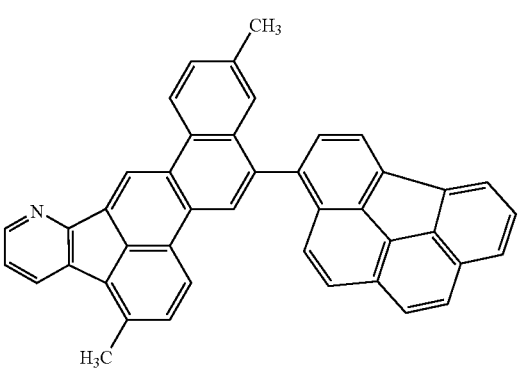

-continued
312
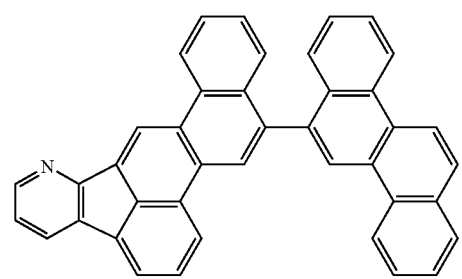
313
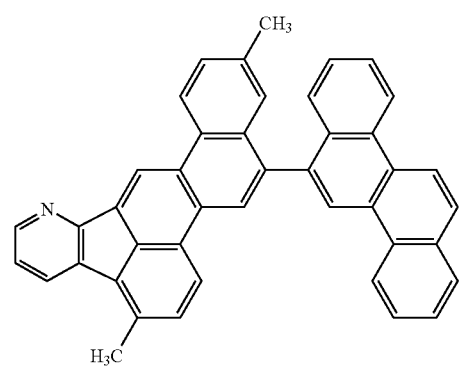
314
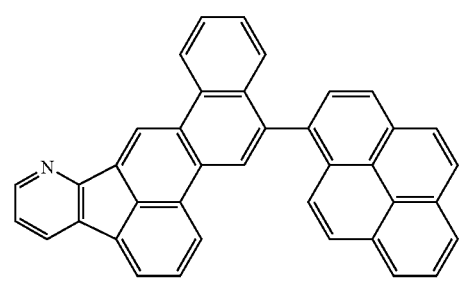
315
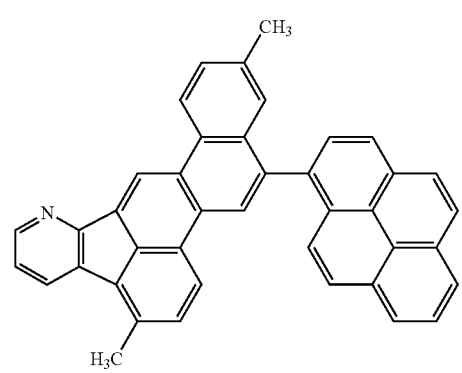
316
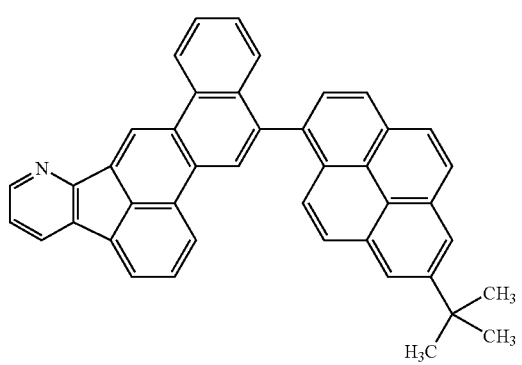
-continued
317
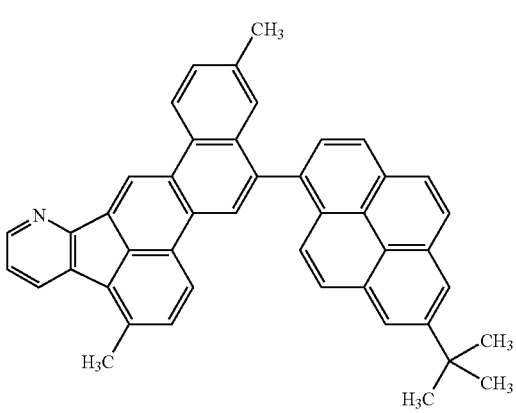
318
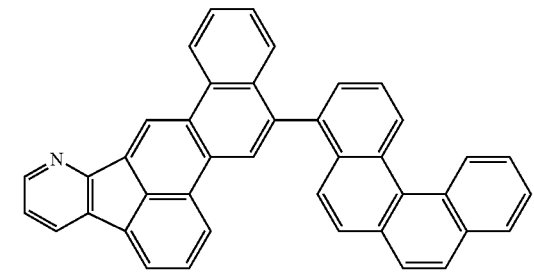
319
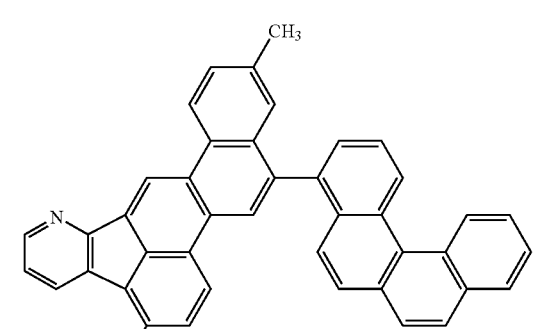
320
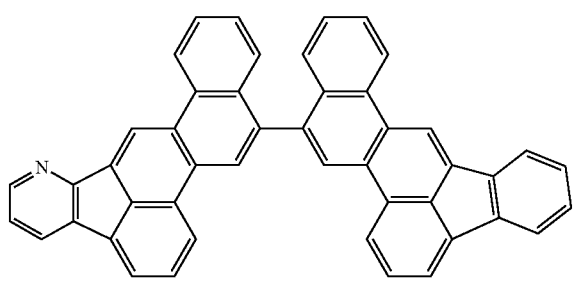

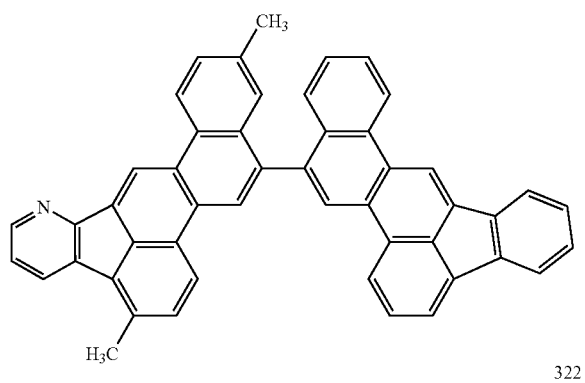
321
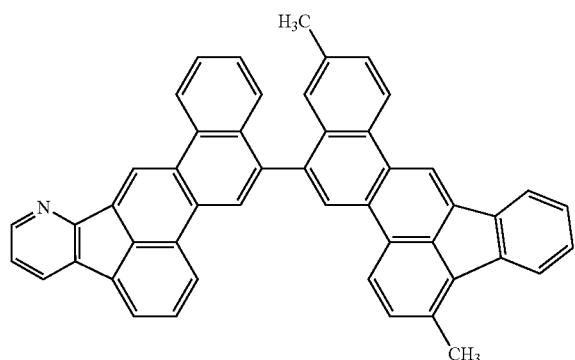
322
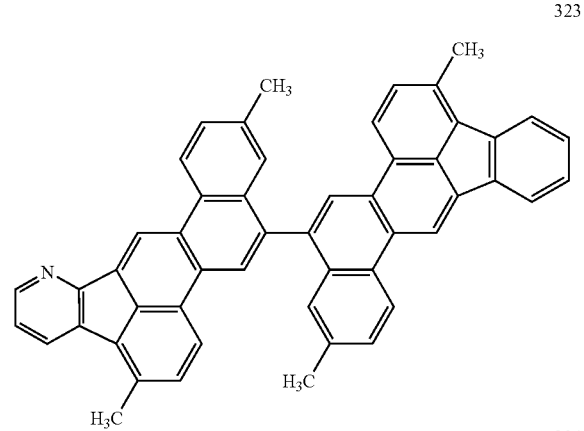
323
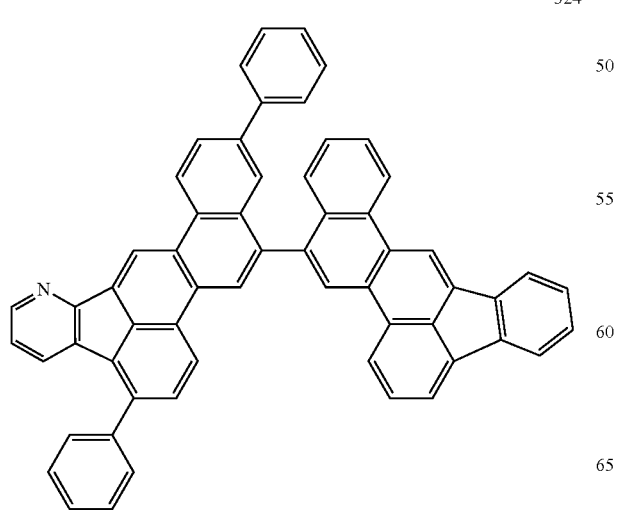
324
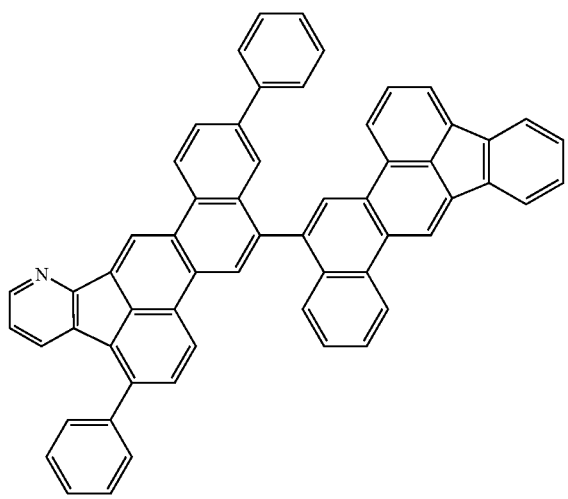
325
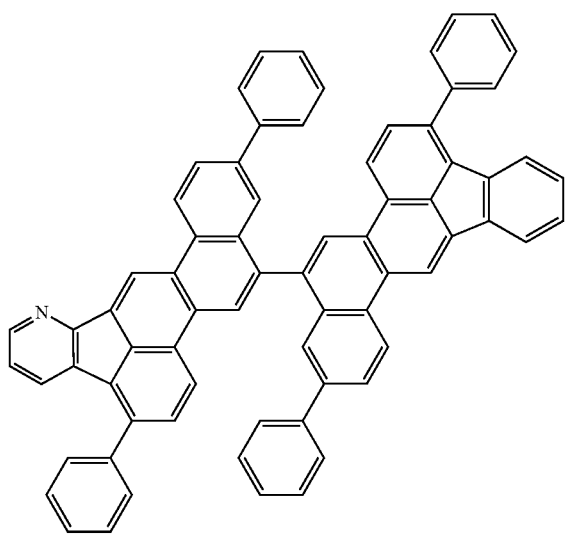
326
COMPOUND EXAMPLE 4
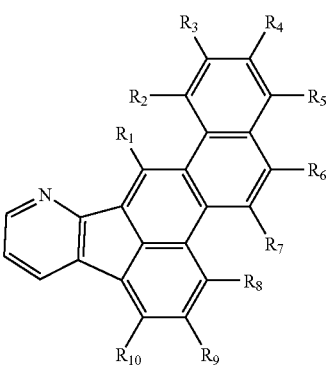
[3]
In this compound example, in General Formula [3] above, $R_6$: a fused heterocyclic group with three or less rings, such as at least one of a quinolyl group and an azafluorenyl group.

$R_1$ to $R_5$ and $R_7$ to $R_{10}$: a hydrogen atom, an alkyl group such as at least one of a methyl group and a tertiary butyl group, or an aryl group such as a phenyl group.
$R_1$ to $R_5$ and $R_7$ to $R_{10}$ may be identical to or different from each other.
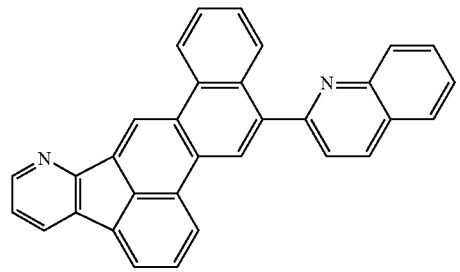
401
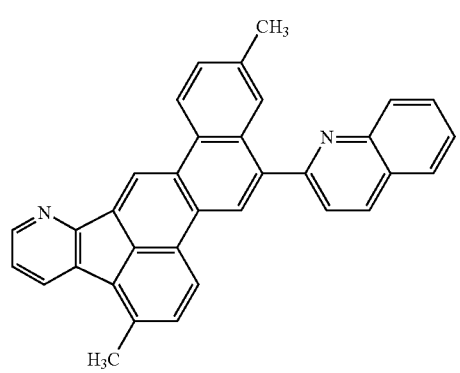
402
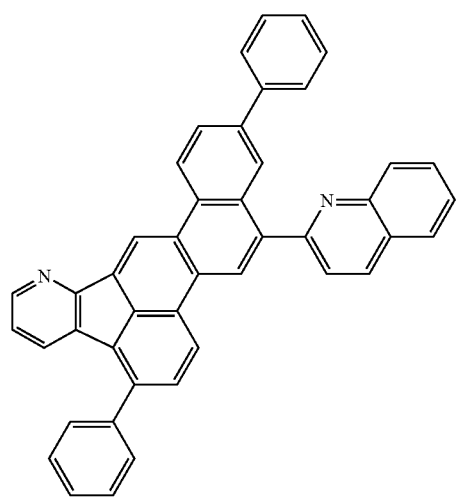
403
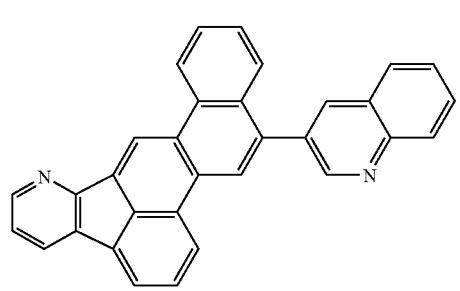
404
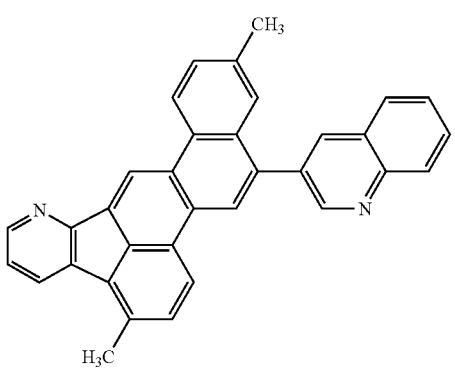
405
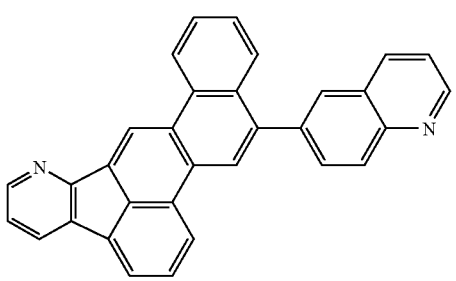
406
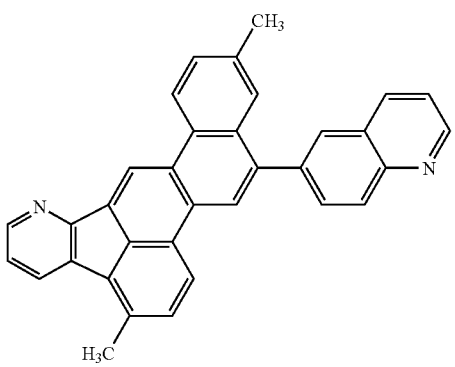
407
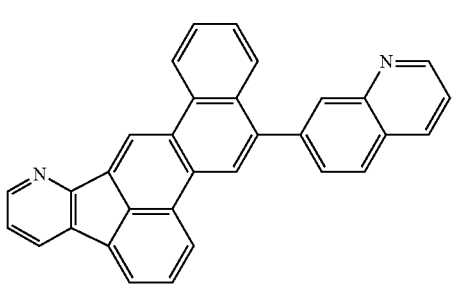
408
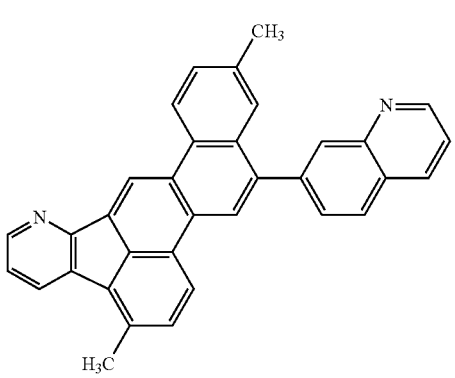
409

410
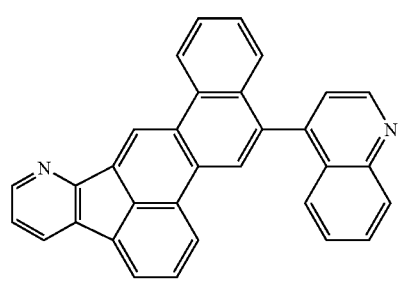
411
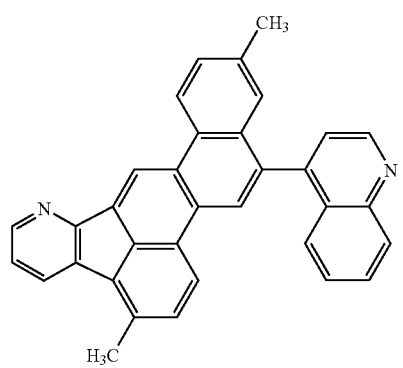
412
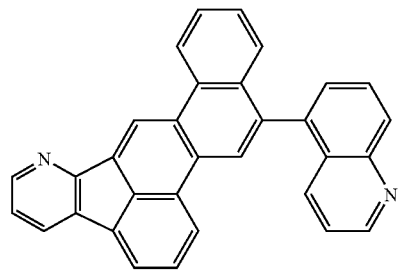
413
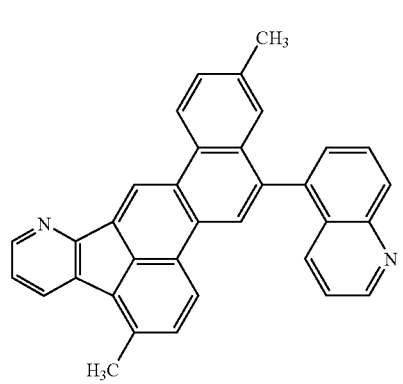
414
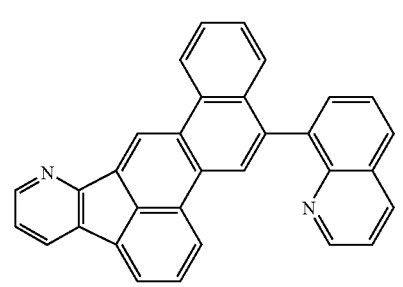
415
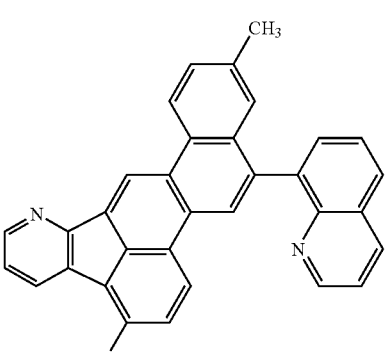
416
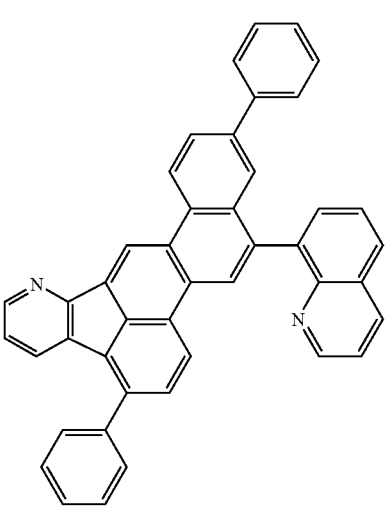
417
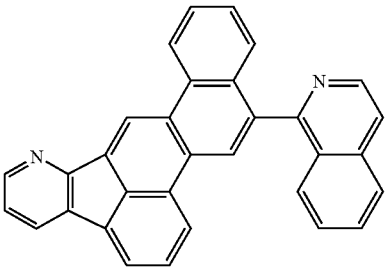
418
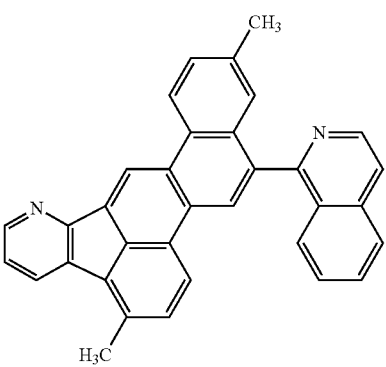

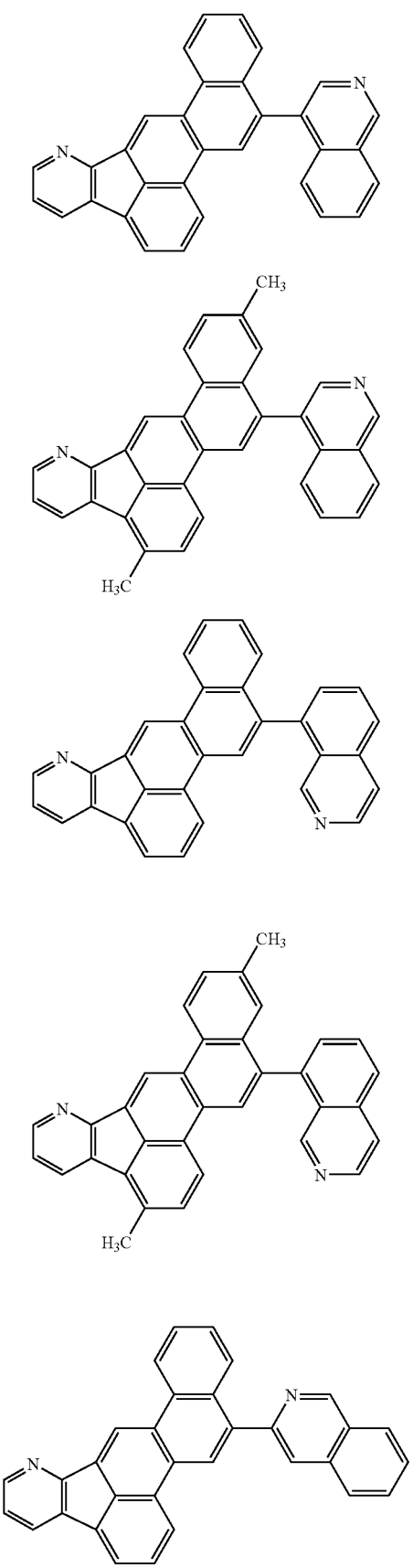
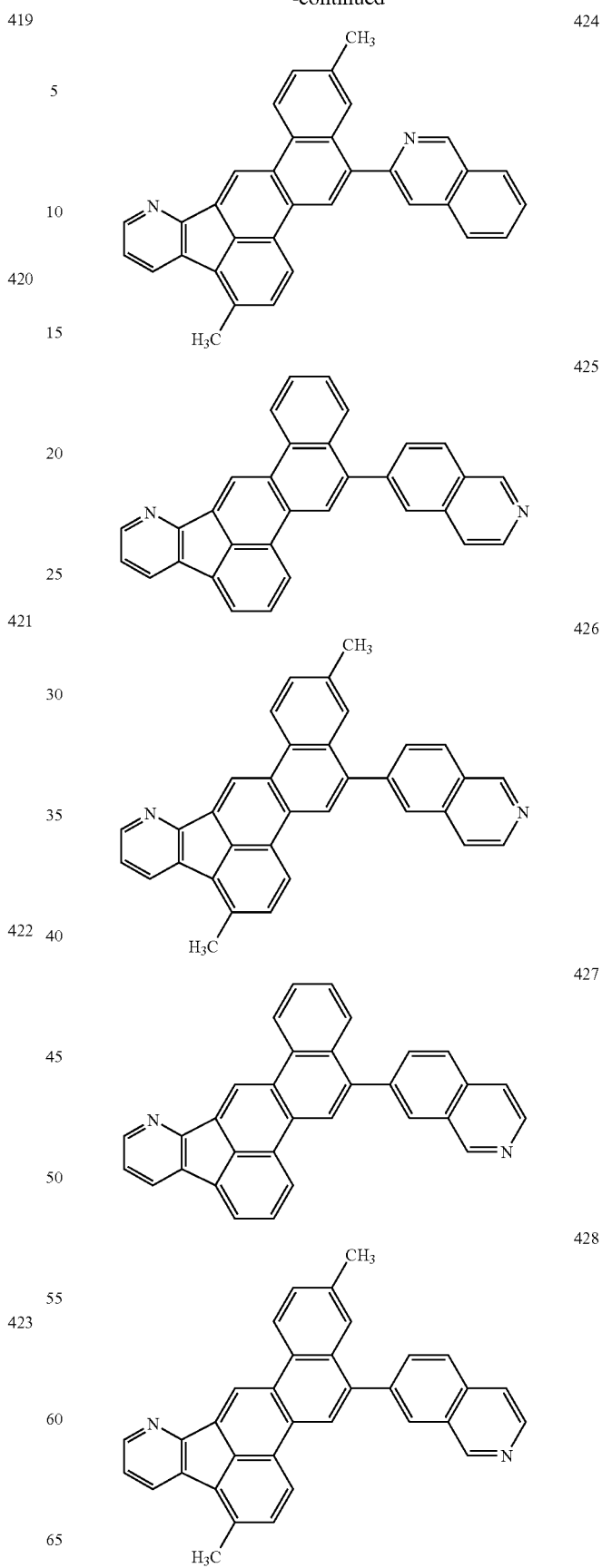

429
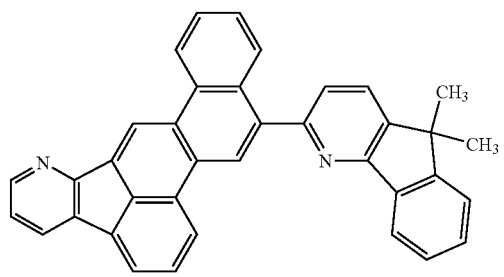
430
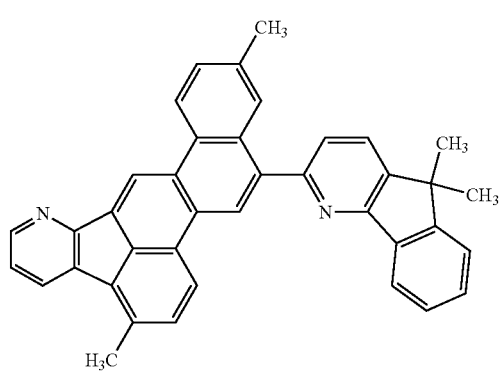
431
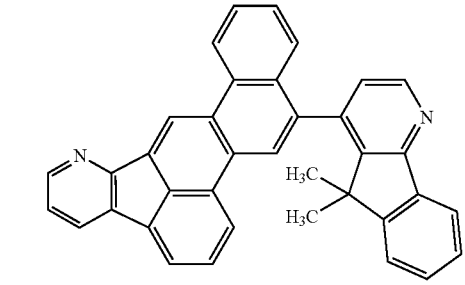
432
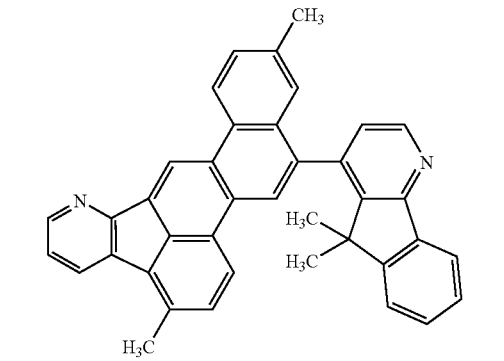
433
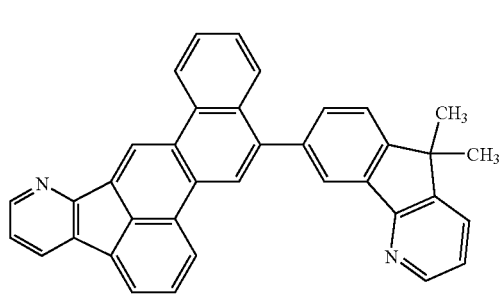
434
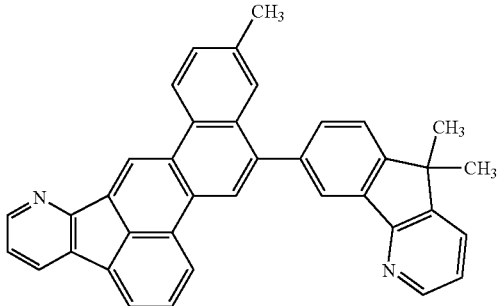
435
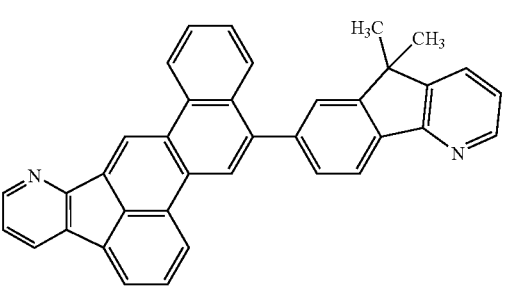
436
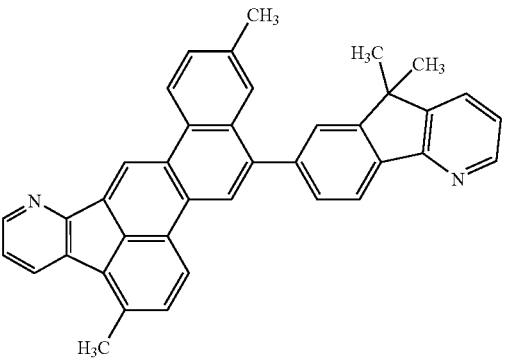
COMPOUND EXAMPLE 5
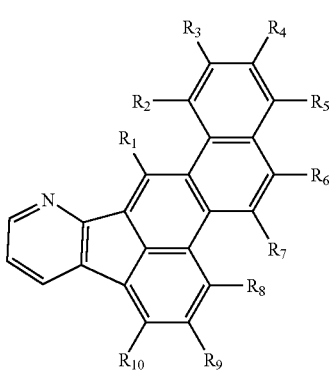
[3]
In this compound example, in General Formula [3] above, $R_6$: a fused heterocyclic group with four or more and five or less rings, such as an azafluoranthenyl group and an azabenzofluorenyl group.

R₁ to R₅ and R₇ to R₁₀: a hydrogen atom, an alkyl group such as at least one of a methyl group and a tertiary butyl group, or an aryl group such as a phenyl group.
R₁ to R₅ and R₇ to R₁₀ may be identical to or different from each other.
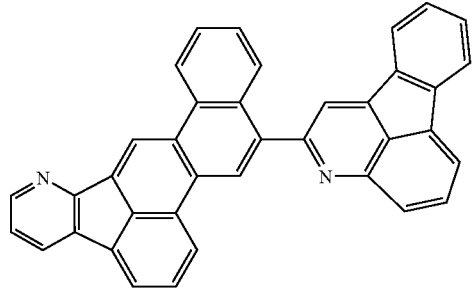
501
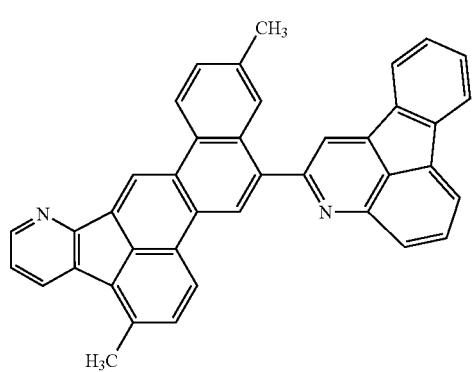
502
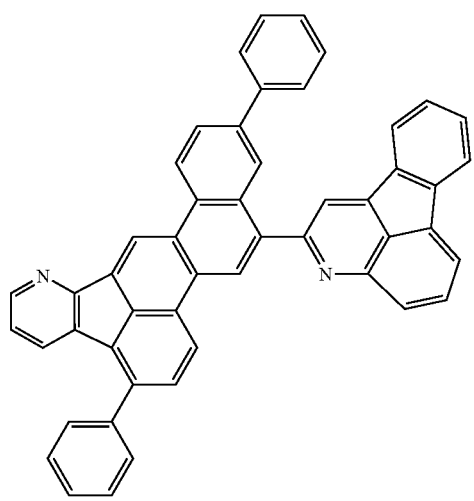
503
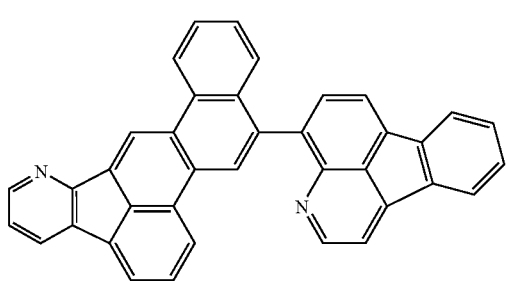
504
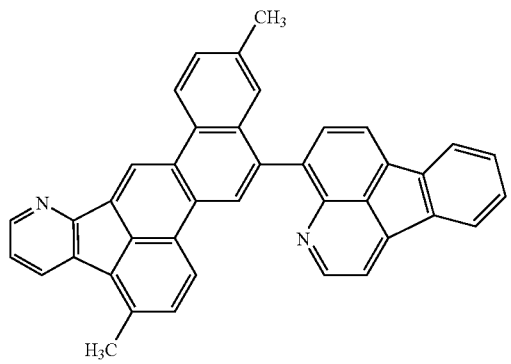
505
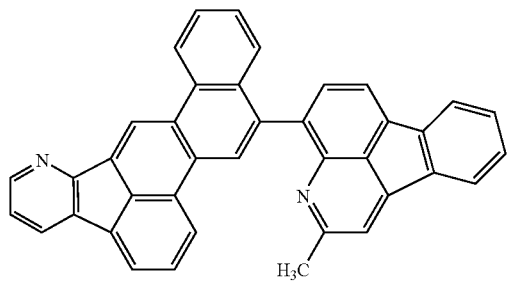
506
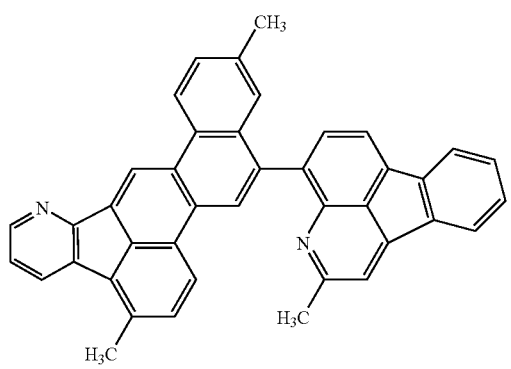
507
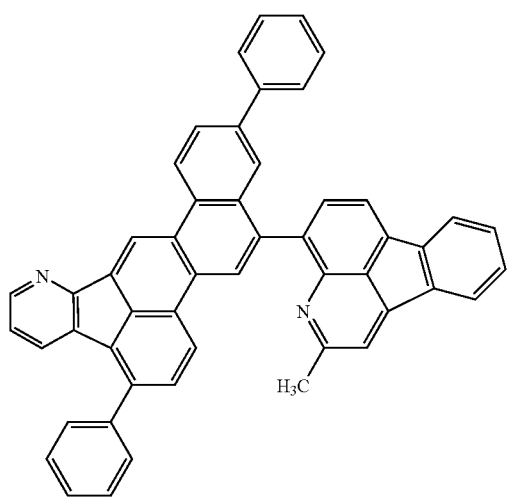
508

509
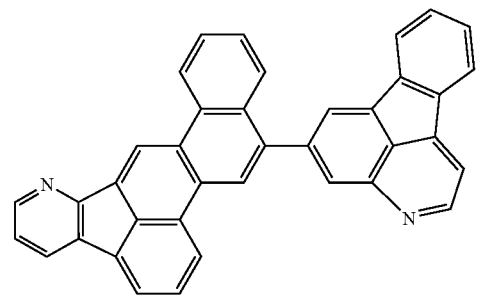
510
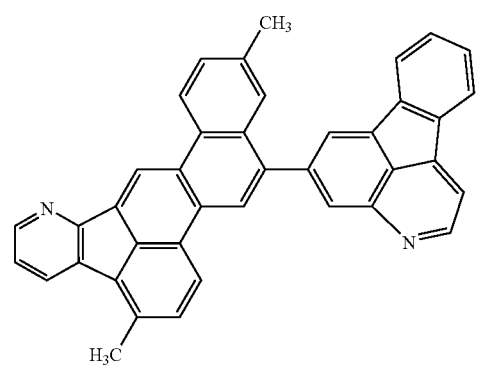
511
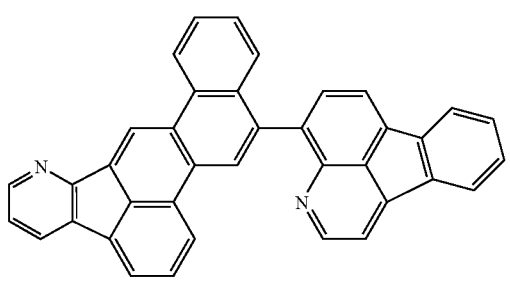
512
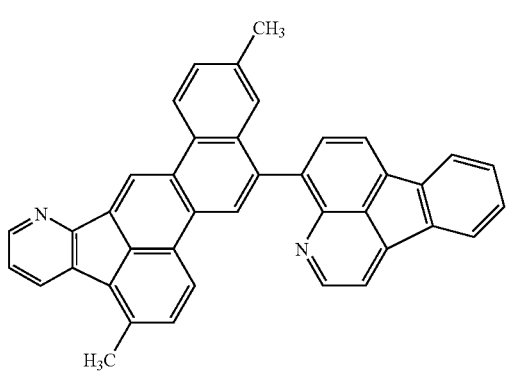
513
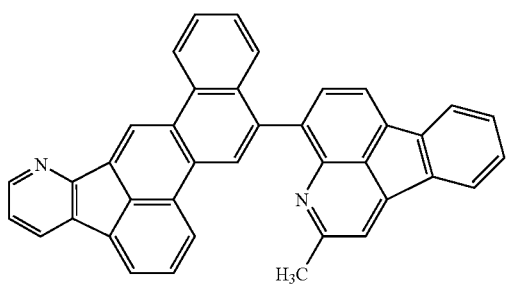
514
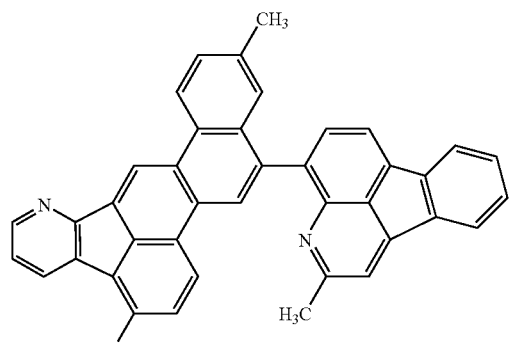
515
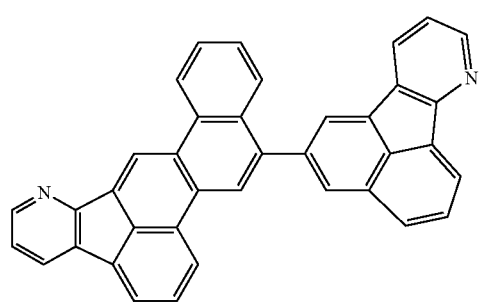
516
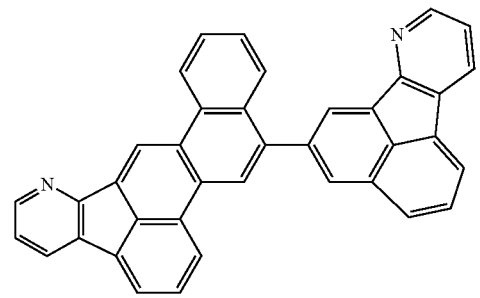
517
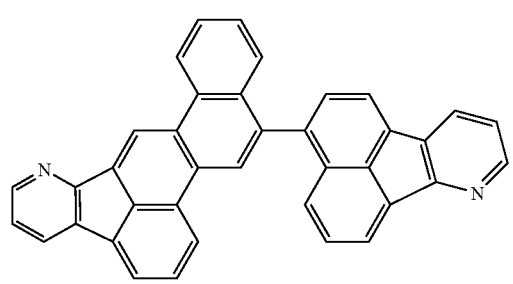
518
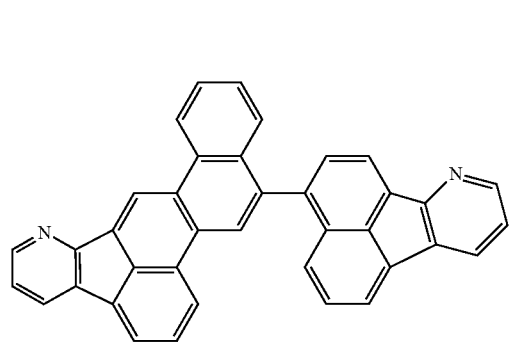

519

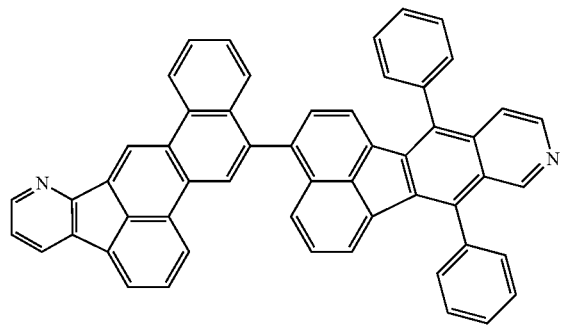

520

521

522

523

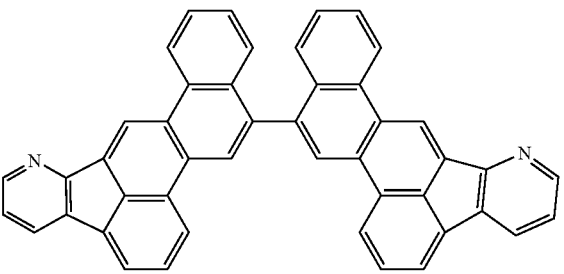

524

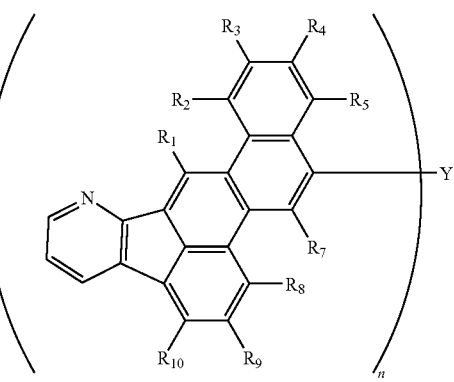

COMPOUND EXAMPLE 6

[4]

In this compound example, in General Formula [4] above,

Y: a linking group with a valence of equal to or greater than 2 and equal to or less than 4 that is derived from an aryl group such as at least one of a phenylene group and a biphenylene group.

$R_1$ to $R_5$ and $R_7$ to $R_{10}$: a hydrogen atom, an alkyl group such as at least one of a methyl group and a tertiary butyl group, or an aryl group such as a phenyl group.

$R_1$ to $R_5$ and $R_7$ to $R_{10}$ may be identical to or different from each other.

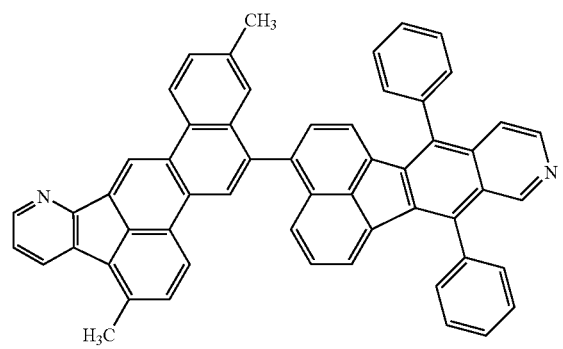

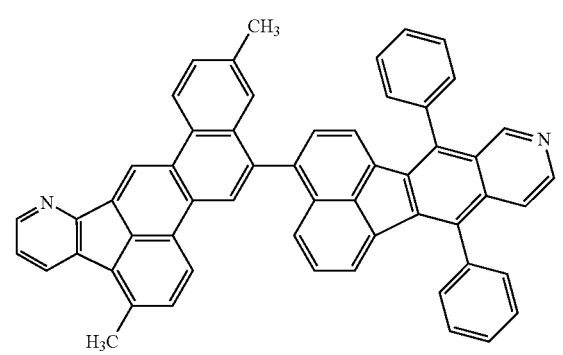

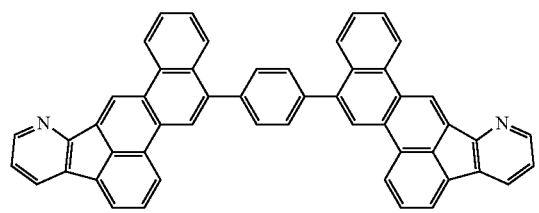
601
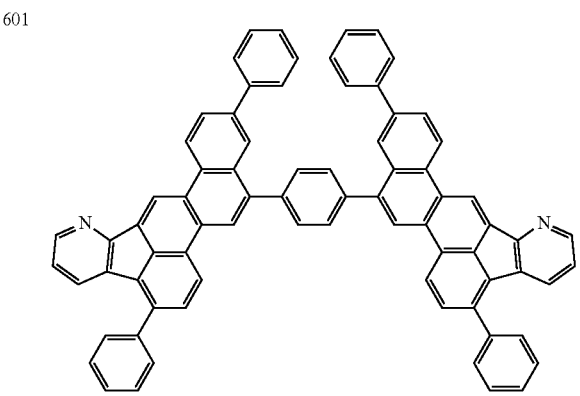
602
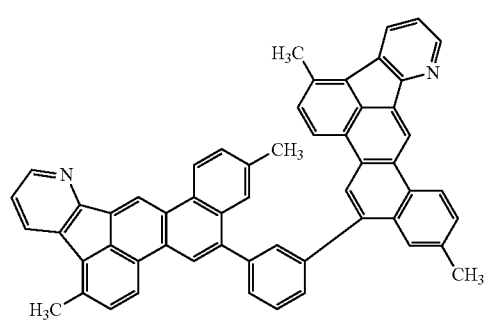
603
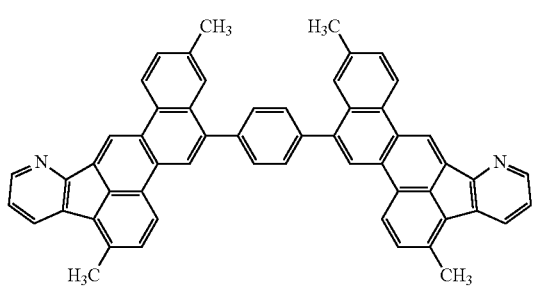
604
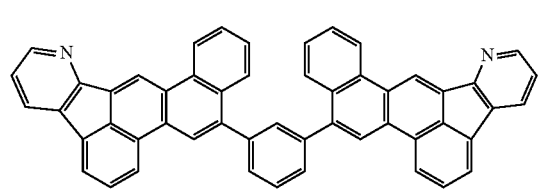
605
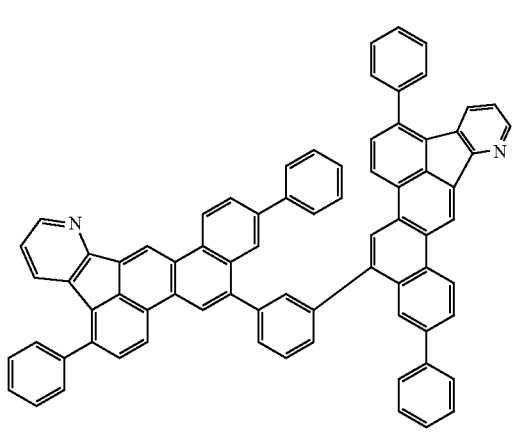
606
607
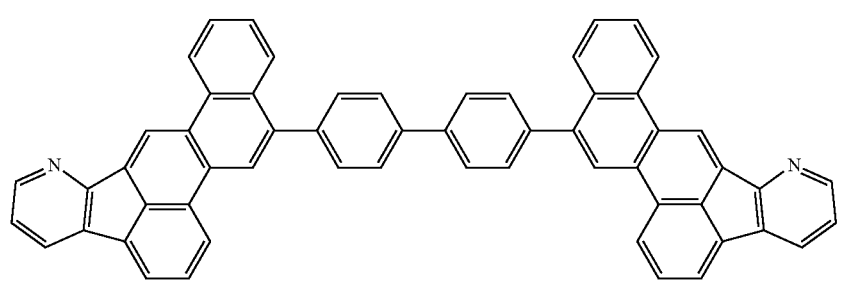

-continued
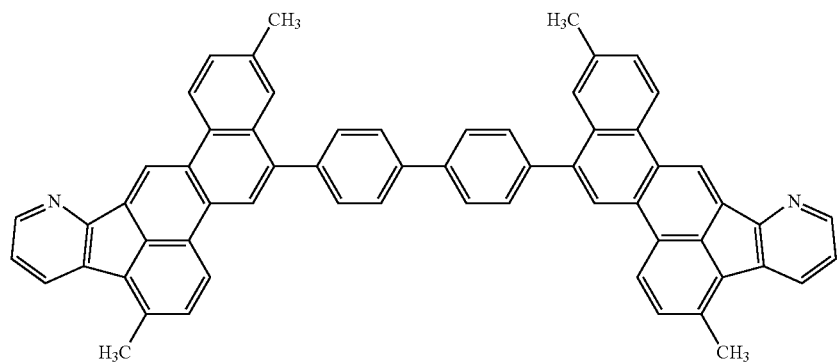
608
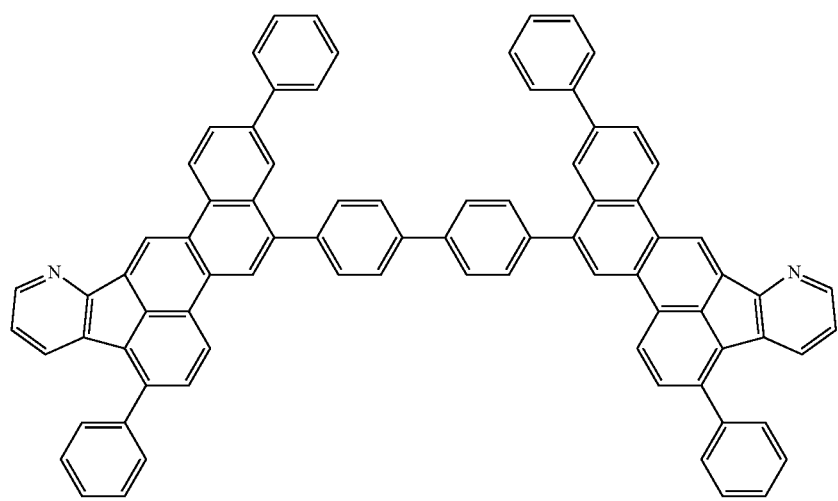
609
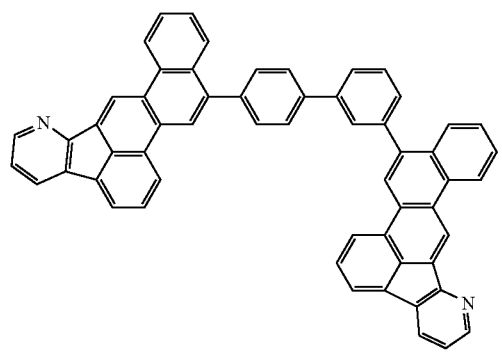
610
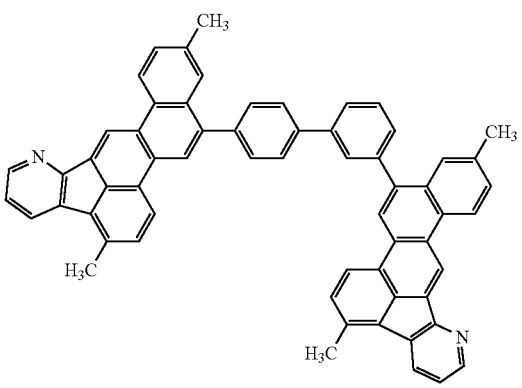
611

-continued

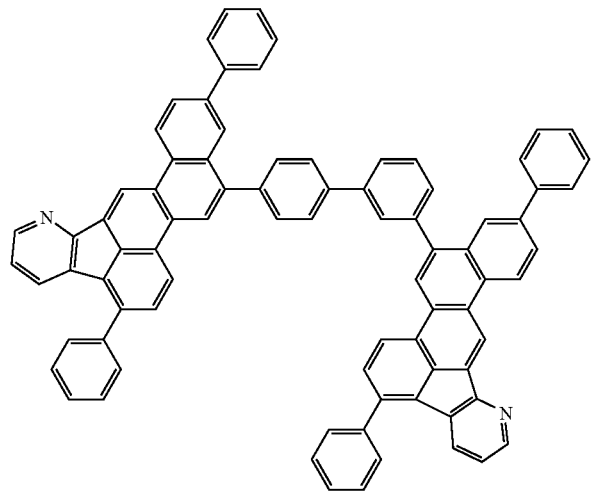
612

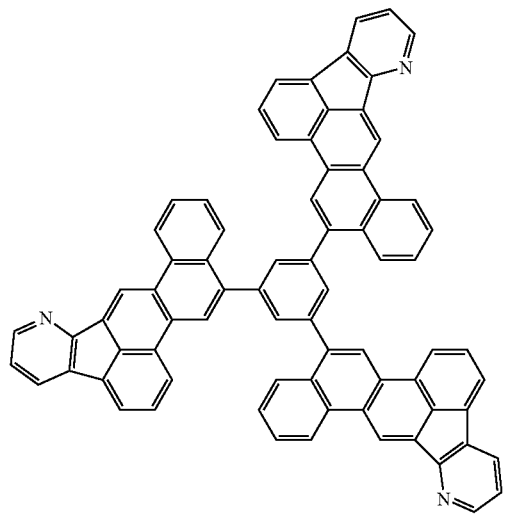
613

COMPOUND EXAMPLE 7

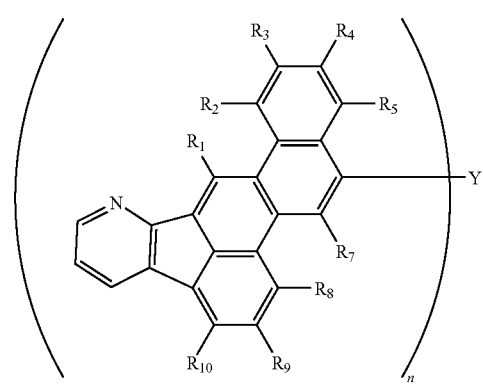
[4]

In this compound example, in General Formula [4] above,

Y: a linking group with a valence of equal to or greater than 2 that is derived from a fused polycyclic aromatic group such as at least one of a naphthylene group, an anthrylene group, and a fluorenylene group.

$R_1$ to $R_5$ and $R_7$ to $R_{10}$: a hydrogen atom, an alkyl group such as at least one of a methyl group and a tertiary butyl group, or an aryl group such as a phenyl group.

$R_1$ to $R_5$ and $R_7$ to $R_{10}$ may be identical to or different from each other.

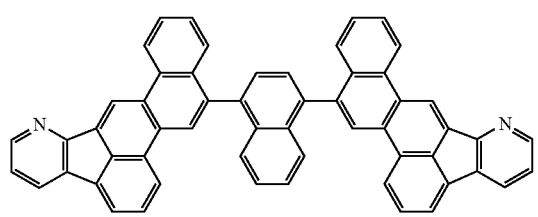
701

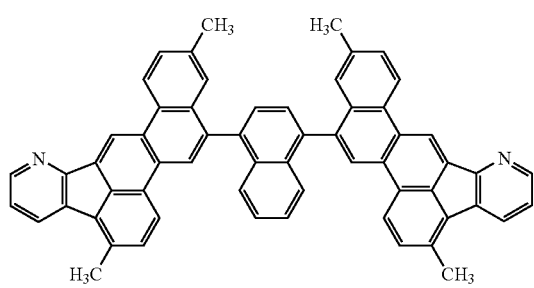
702

-continued
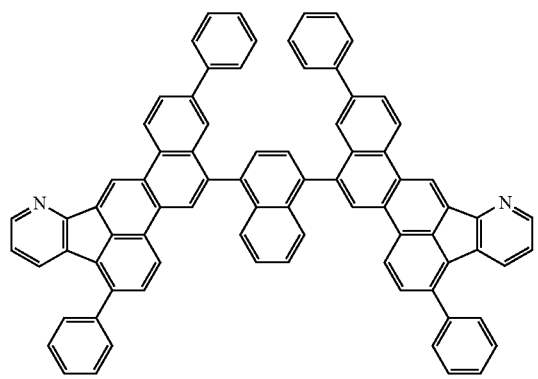
703
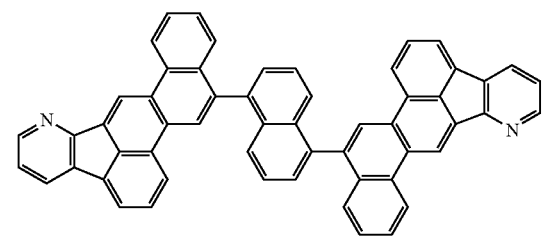
704
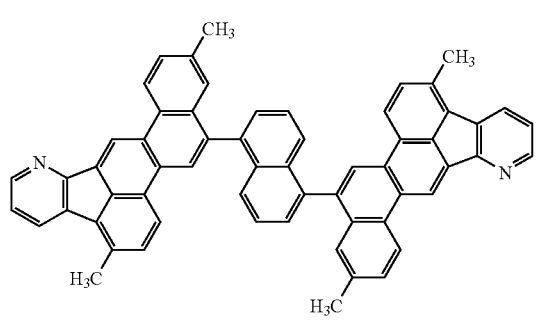
705
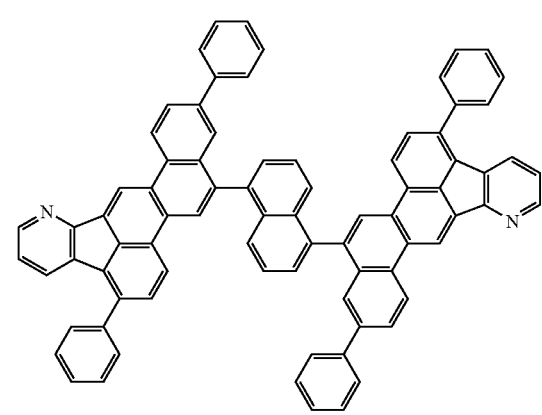
706
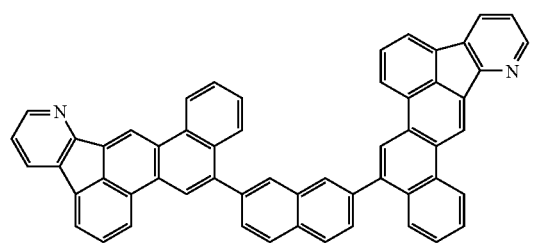
707
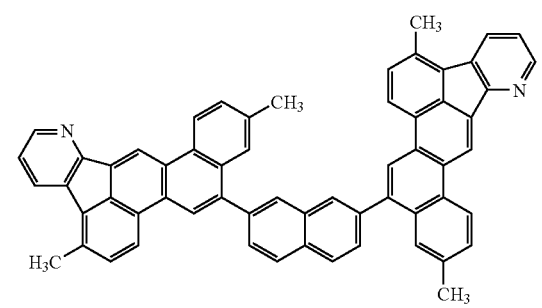
708
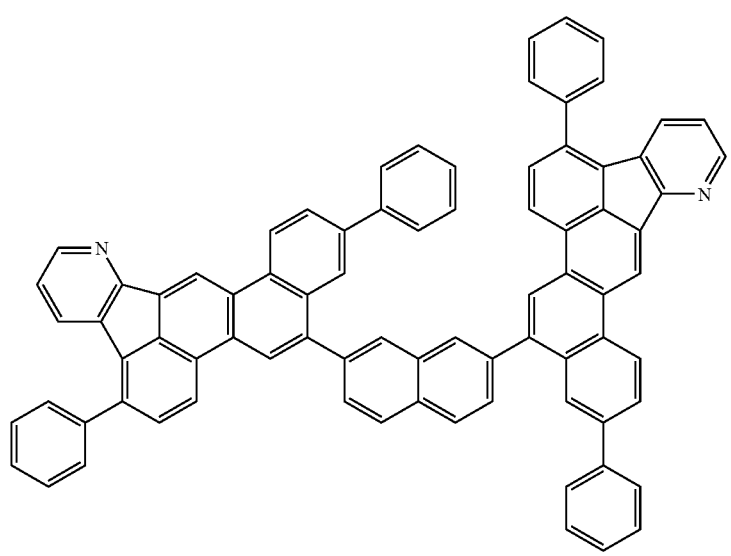
709

-continued
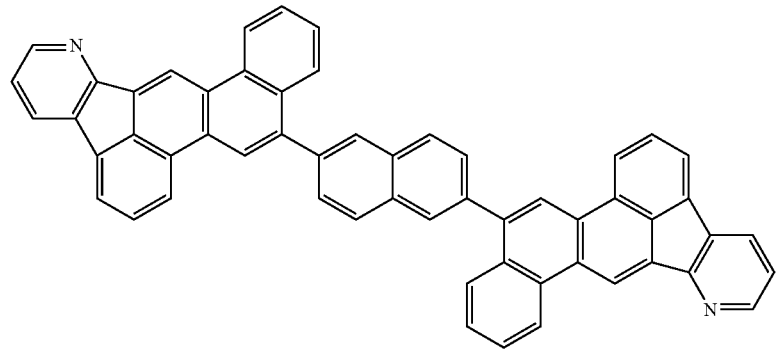
710
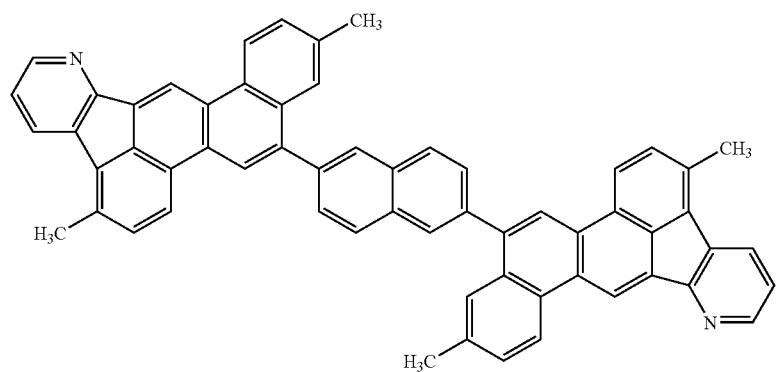
711
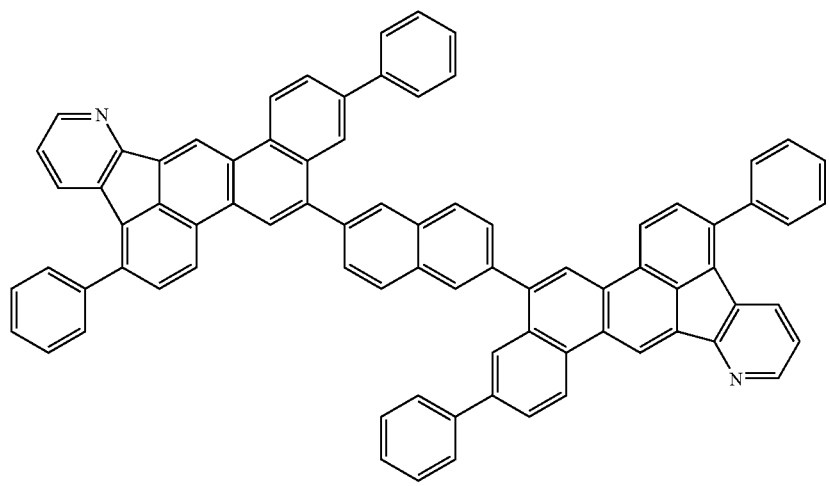
712
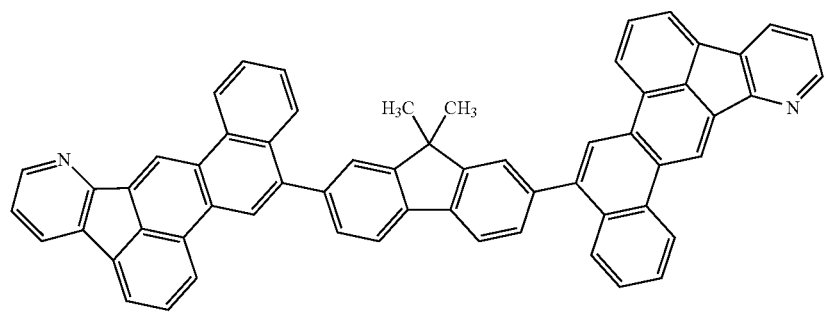
713

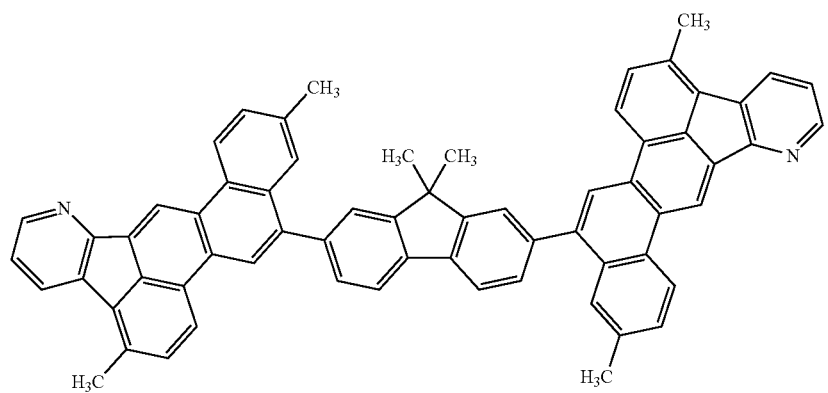
714
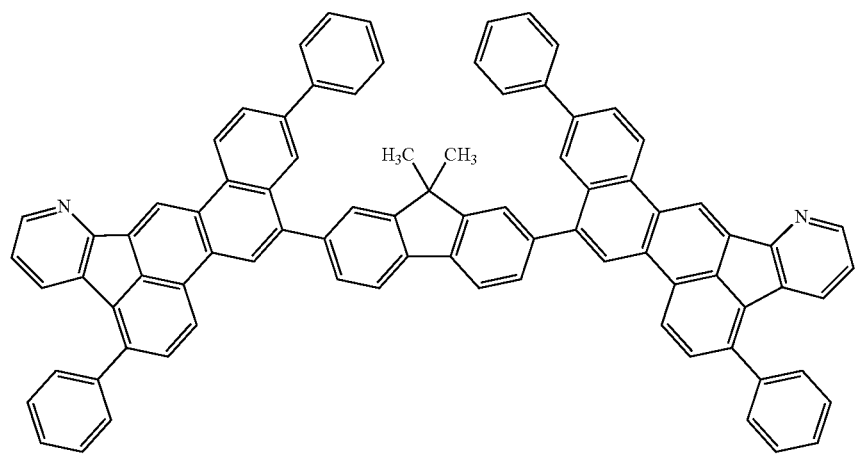
715
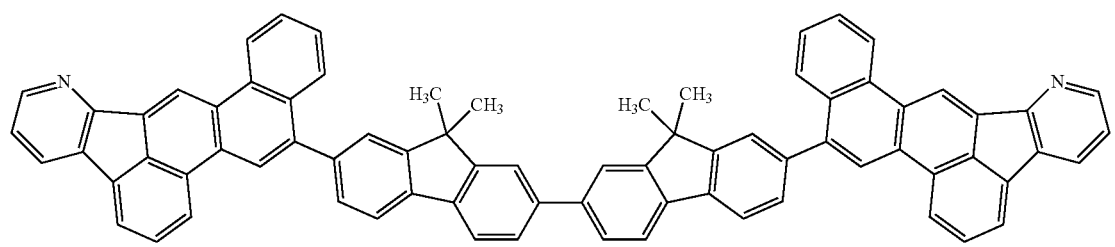
716
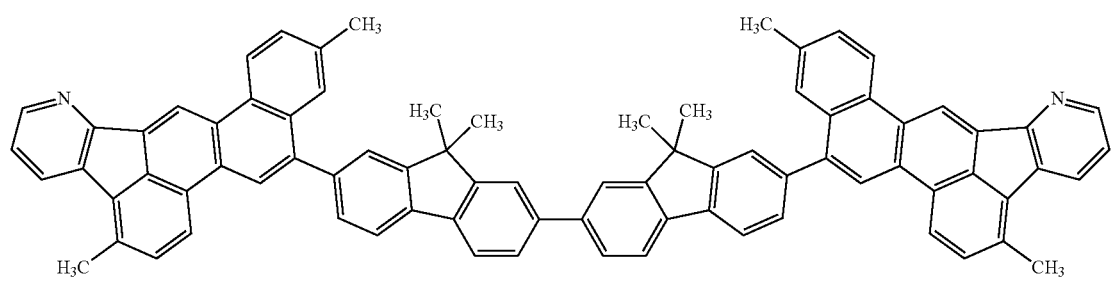
717

-continued
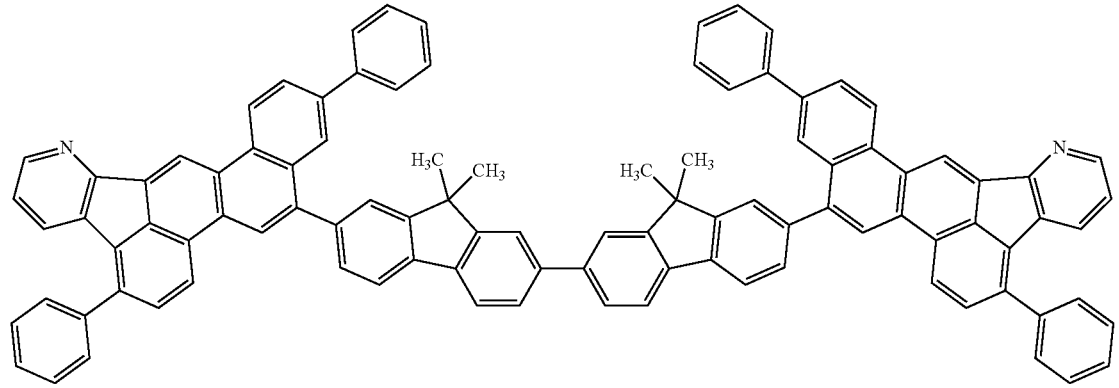
718
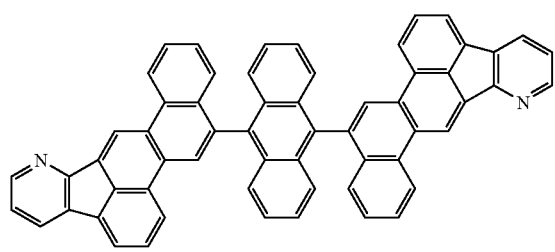
719
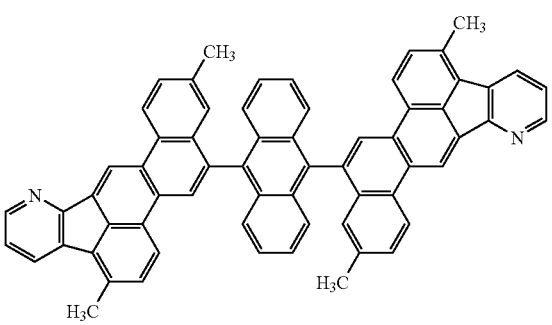
720
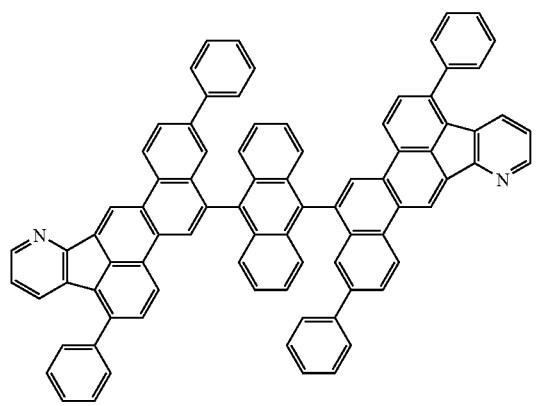
721
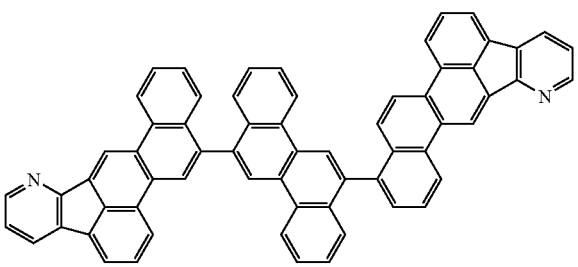
722
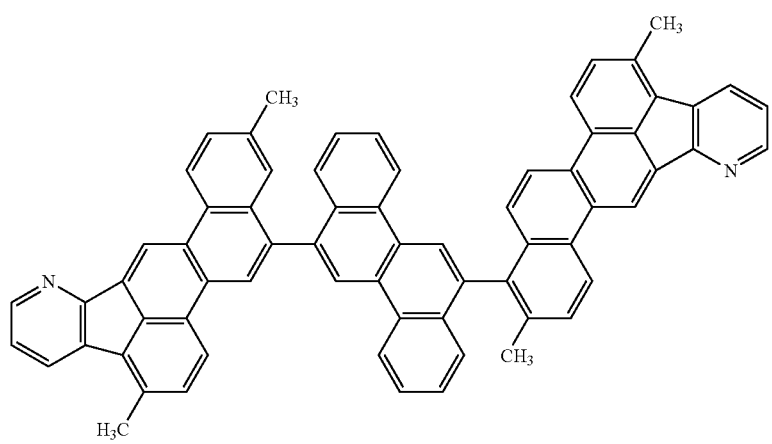
723

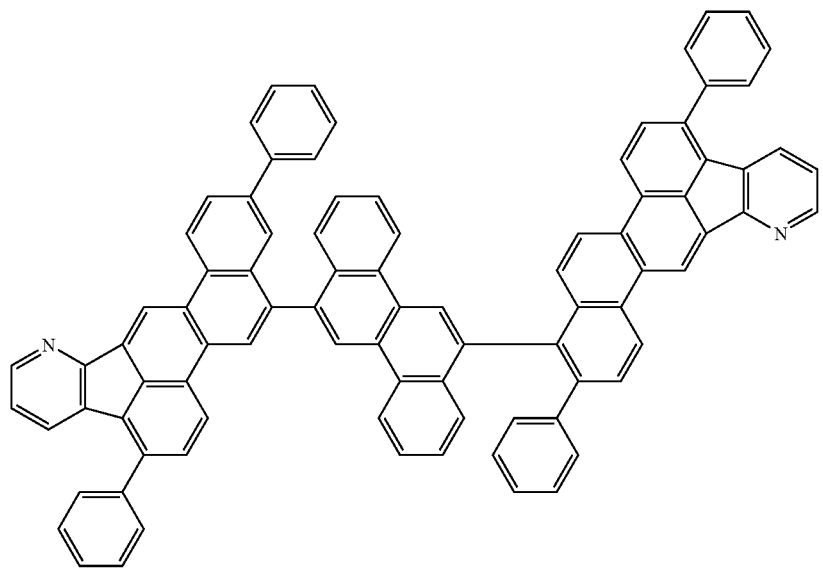

724

The organic light-emitting device of the present invention will be described below in more detail.

The organic light-emitting device of the present invention comprises a pair of electrodes comprising an anode and a cathode and at least one organic compound layer sandwiched (disposed) between the pair of electrodes. The organic compound layer includes at least one kind of the organic compound of the present invention. Further, either of the anode and cathode is transparent or semi-transparent.

The organic compound layer may comprise a single layer or a plurality of layers. In a case where the organic compound layer comprises a plurality of layers, the layers may comprise functionally separated functional layers. A specific example of the layer configuration of the organic light-emitting device is shown below.

The first specific example relates to an organic light-emitting device that has a structure in which a substrate, an anode, a light-emitting layer, and a cathode are provided in the order of description.

The second specific example relates to an organic light-emitting device that has a structure in which a substrate, an anode, a hole transport layer, an electron transport layer, and a cathode are provided in the order of description. In this case, the light-emitting layer is the hole transport layer and the electron transport layer.

The third specific example relates to an organic light-emitting device that has a structure in which a substrate, an anode, a hole transport layer, a light-emitting layer, an electron transport layer, and a cathode are provided in the order of description.

The fourth specific example relates to an organic light-emitting device that has a structure in which a substrate, an anode, a hole injection layer, a hole transport layer, a light-emitting layer, an electron transport layer, and a cathode are provided in the order of description.

The fifth specific example relates to an organic light-emitting device that has a structure in which a substrate, an anode, a hole transport layer, a light-emitting layer, a hole/exciton blocking layer, an electron transport layer, and a cathode are provided in the order of description.

As shown in the examples above, the organic compound layer disposed between the anode and cathode may comprise various functional layers. Further, the compound of the invention may be included in at least anyone of these functional layers, or a specific functional layer may have a plurality of compounds of the invention.

However, these layer structures show a basic device structure, and the structure of the organic light emitting device of the present invention is not limited to thereto. For example, the organic light emitting device of the present invention may have any one of various layer structures containing: a structure in which an insulating layer is provided at an interface between an electrode and an organic layer; a structure in which an adhesive layer or interference layer is provided; and a structure in which a hole transport layer is composed of two layers with different ionization potentials.

The azaindenochrysene derivative may be provided in at least any one of the light-emitting layer, electron transport layer, and hole transport layer. For example, the azaindenochrysene derivative may be contained in the light-emitting layer. The light-emitting layer may comprise a host and a guest.

In a case where the azaindenochrysene derivative is used as a material for the organic light-emitting device comprising the light-emitting layer, the azaindenochrysene derivative can be used independently or can be used as a dopant (guest) material or host material.

In a case where the light-emitting layer comprises a host material that has carrier transport property and a guest, the following several processes are involved in light emission.
1. the transport of an electron or a hole in the light emission layer;
2. the generation of an exciton of the host;
3. the transfer of excitation energy between host molecules; and
4. the transfer of excitation energy from the host to the guest.

The desired energy transfer or light emission in each process competes with various deactivation processes.

It is needless to say that an improvement in luminous efficiency of an EL device involves a material that is itself mainly responsible for light emission to have a large light emission quantum yield. However, how efficiently energy can be transferred between hosts or between a host and a guest is also of concern. In addition, no cause for the degradation of light emission due to energization has been revealed at present. However, the degradation is assumed to be related to at least the material itself that is mainly responsible for light emission or a change in environment surrounding the luminescent material due to a molecule around the material.

When the azaindenochrysene derivative represented by General Formulas [1] and [2] is particularly used as the host or the guest of the light-emitting device, the color purity of the organic light-emitting device is enhanced, the device emits light with high efficiency, maintains high luminance for a long time period, and shows small degradation of light emission due to energization.

Ina case where the azaindenochrysene derivative represented by General Formulas [1] and [2] is used as a host, the content thereof may be 20 wt. % to 99.9% based on the entire weight of the material constituting the light-emitting layer.

In a case where the azaindenochrysene derivative represented by General Formulas [1] and [2] is used as a dopant (guest), the concentration of dopant in the host material may be 0.01 wt. % to 80 wt. %, preferably 1 wt. % to 40 wt. %. A guest material may be incorporated into the entirety of a layer formed of a host material uniformly or with a concentration gradient. Alternatively, the guest material may be partially incorporated into a certain region of the host material layer so that a region of the layer free of the guest material is present.

It may be the case that the energy gap of the host material is wider than the energy gap of the dopant.

The organic light-emitting device according to embodiments of the present invention uses the azaindenochrysene derivative represented by General Formulas [1] and [2] in particular as a material constituting the light-emitting layer. Further, in addition to the azaindenochrysene derivative, a conventionally known additive compound such as a hole transporting compound of a low molecular weight compound or polymer compound, luminescent compound, or electron transporting compound can optionally be used together.

Examples of these compounds are described below.

A hole-injection transporting material may have excellent mobility for facilitating injection of a hole from an anode and for transporting the injected hole to a light emitting layer. Examples of low-molecular and polymer materials that have hole injection and transport ability include triarylamine derivatives, phenylenediamine derivatives, triazole derivatives, oxadiazole derivatives, imidazole derivatives, pyrazoline derivatives, pyrazolone derivatives, oxazole derivatives, fluorenone derivatives, hydrazone derivatives, stilbene derivatives, phthalocyanine derivatives, porphyrin derivatives, poly(vinyl carbazole), poly(silylene), polythiophene, and other conductive polymers, but this list is specifically not limiting.

In addition to the above-described azaindenochrysene derivatives, examples of light-emitting materials include the following compounds: polycyclic fused aromatic compounds (naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, rubrene, etc.), quinacridone derivatives, acridone derivatives, coumarin derivatives, pyran derivatives, Nile red, pyrazine derivatives, benzimidazole derivatives, benzothiazole derivatives, benzoxazole derivatives, stilbene derivatives, organic metal complexes (for example, organic aluminum complexes such as tris(8-quinolinolate)aluminum and organic beryllium complexes), and polymer derivatives such as poly(phenylene vinylene) derivatives, poly(fluorene) derivatives, and poly (phenylene) derivatives, poly(thienylene vinylene), but this list is specifically not limiting.

The electron-injection transporting material may be arbitrarily selected from materials which facilitate injection of an electron from a cathode and which have a function of transporting the injected electron into a light emitting layer. The material is selected in consideration of, for example, the balance with the mobility of a carrier of the hole transport material. Examples of materials having an electron injection and transport property include oxadiazole derivatives, oxazole derivatives, triazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organic metal complexes. This list is specifically not limiting.

Other materials constituting the organic light-emitting device of the present invention are described below.

A material with as large a work function as possible may be used as the anode material. For example, simple substance of metals such as gold, platinum, silver, copper, nickel, palladium, cobalt, selenium, vanadium, and tungsten, alloys thereof, and metal oxides such as tin oxide, zinc oxide, indium oxide, indium tin oxide (ITO), and indium zinc oxide can be used. Electrically conductive polymers such as polyaniline, polypyrrole, polythiophene, and polyphenylene sulfide can be also used. These electrode substances may be used individually or in combinations of a plurality thereof. Further, the anode may have a single layer structure or a multilayer structure.

Meanwhile a material with as small a work function as possible may be used as the cathode material. For example, metals such as lithium, sodium, potassium, calcium, magnesium, aluminum, indium, ruthenium, titanium, manganese, yttrium, silver, lead, tin, and chromium, or alloys in which these metals are combined may be used as the cathode material. For example, lithium-indium, sodium-potassium, magnesium silver, aluminum, lithium, aluminum magnesium, and magnesium indium alloys can be used. Metal oxides such as indium tin oxide (ITO) can be also used. These electrode substances may be used individually or in combinations of a plurality thereof. Further, the anode may have a single layer structure or a multilayer structure.

The substrate used in the organic electron-emitting device of the present invention is not particularly limited, and a non-transparent substrate such as a metal substrate and a ceramic substrate or a transparent substrate such as glass, quartz, and a plastic sheet can be used. Further, a color filter film, a fluorescent color converting filter film, a dielectric reflection film, or the like may be used in the substrate for controlling luminescent color.

Further, a protective layer or a sealing layer may be formed on the produced device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, or a polystyrene resin; and a photo-curable resin. Further, the device itself may be covered with glass, a gas impermeable film, a metal, or the like and packaged with an appropriate sealing resin.

A thin-film transistor (TFT) can be provided on the substrate, and the device of the present invention may be connected to TFT.

Regarding the emission direction of a device, the device may have a bottom emission structure (structure in which light is emitted from a substrate side) or a top emission structure (structure in which light is emitted from an opposite side of the substrate).

In the light-emitting device of the present invention, the layer containing the azaindenochrysene derivative and layers containing other organic compounds can be formed by the following methods. A thin film is generally formed by vacuum deposition method, an ionized evaporation method, sputtering and plasma. In particular, a layer formed by a vacuum deposition method or a solvent coating method is preferred because crystallization hardly occurs and excellent long-term stability is obtained.

A thin film may be also formed by dissolving in an appropriate solvent and using a well-known coating method (for example, spin coating, dipping, casting method, LB method, and ink jet method). In particular, when a film is formed by the coating method, the film can be formed by combining the film material with an appropriate binder resin.

The binder resin can be selected from a wide range of resins having binder properties. Examples of suitable resins include polyvinyl carbazole resins, polycarbonate resins, polyester resins, polyarylate resins, polystyrene resins, ABS resins, polybutadiene resins, polyurethane resins, acrylic resins, methacrylic resins, butyral resins, polyvinyl acetate resins, polyamide resins, polyimide resins, polyethylene resins, polyethersulfone resins, diallylphthalate resins, phenolic resins, epoxy resins, silicone resins, polysulfone resins, and urea resins, but this list is not limiting. These resins may be used alone or in a mixture of two or more kinds thereof as a homopolymer or copolymer. If necessary, well-known additives such as a plasticizer, an antioxidant, and an ultraviolet absorber may be added.

EXAMPLES

Hereinafter, the present invention will be described more specifically by way of examples, but the present invention is not limited to these examples.

EXAMPLE 1

Method for Producing Exemplified Compound No. 304

The Exemplified Compound 304 of the present invention can be produced, for example, by such a method as described below.

(1) Synthesis of Intermediate Compound 1

Chrysene was used as a starting material and Intermediate Compound 1 was obtained by a method represented by the following reaction formula [1] with reference to the synthesis method described in Tetrahedron Letters 1992, 33, 1675 (non-patent document).

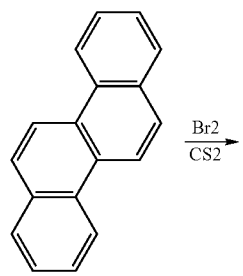

[1]

-continued

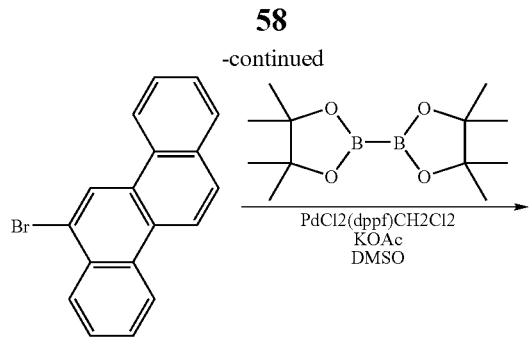

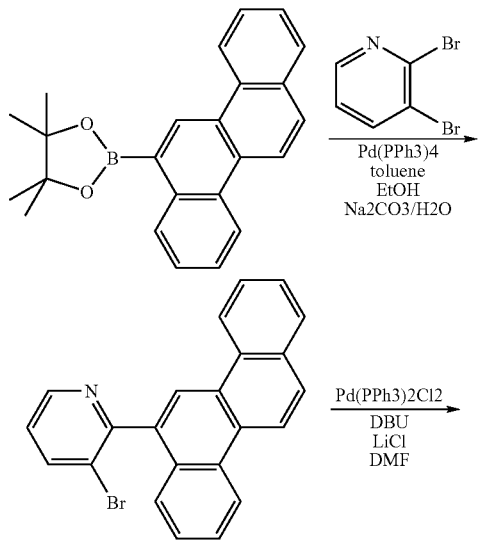

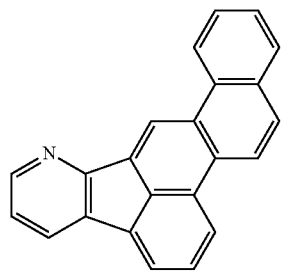

Intermediate Compound 1

304.4 as M+ of the compound was confirmed by MALDI-TOF MS (Matrix Assisted Laser Desorption/Ionization—Time-of-Flight Mass Spectrometry).

$^1$H-NMR (CDCl$_3$): δ (ppm)=9.64 (s, 1H), 9.02 (d, 1H, J=8.69 Hz), 8.74 (d, 1H, J=8.69 Hz), 8.68-8.66 (m, 2H), 8.22 (dd, 1H, J$_1$=7.78 Hz, J$_2$=1.37), 8.10 (dd, 2H, J$_1$=13.95 Hz, J$_2$=8.01), 8.05 (dd, 1H, J$_1$=8.23 Hz, J$_2$=1.37), 7.88 (dd, 1H, J$_1$=8.46 Hz, J$_2$=7.09), 7.81-7.77 (m, 1H), 7.69 (td, 1H, J$_1$=7.43 Hz, J$_2$=1.07), 7.34 (d, 1H, J$_1$=7.78 Hz, J$_2$=5.03).

A PL spectrum of a toluene solution (1.0×10$^{-5}$ mol/L) of the Intermediate Compound 1 was measured, and a blue emission spectrum having an emission peak at 442 nm and a half-width of 95 nm was obtained (FIG. 1).

(2) Synthesis of Intermediate Compound 2

The Intermediate Compound 1 obtained according to the reaction formula [1] was used as a starting material, and Intermediate Compound 2 was obtained by a method represented by the following reaction formula [2].

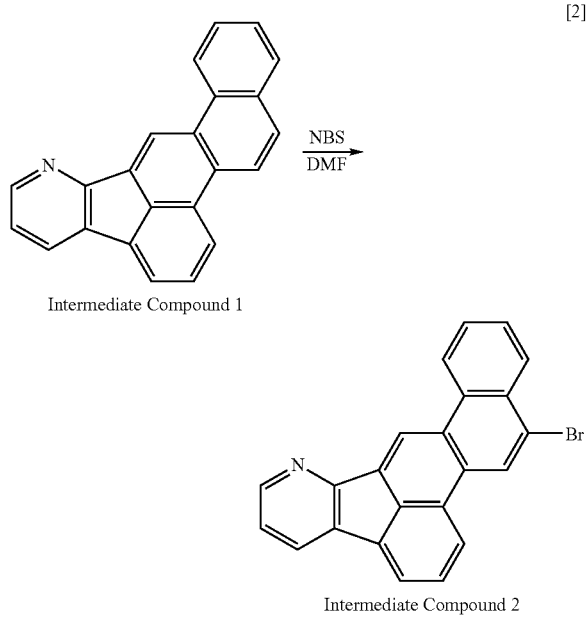

Intermediate Compound 1

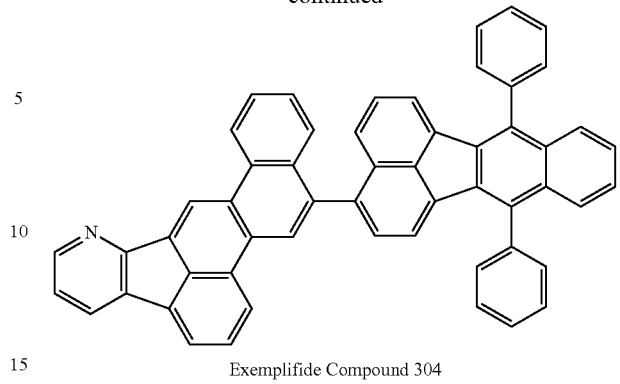

Exemplified Compound 304

382.4 as M⁺ of the compound was confirmed by MALDI-TOF MS (Matrix Assisted Laser Desorption/Ionization—Time-of-Flight Mass Spectrometry).

$^1$H-NMR (DMSO): δ (ppm)=9.53 (s, 1H), 9.15 (s, 1H), 8.99 (dd, 1H, $J_1$=9.21 Hz, $J_2$=1.60), 8.85 (d, 1H, J=8.41 Hz), 8.72 (dd, 1H, $J_1$=5.21 Hz, $J_2$=1.20), 8.62 (dd, 1H, $J_1$=7.61 Hz, $J_2$=1.20), 8.34-8.31 (m, 1H), 8.30 (d, 1H, J=7.21 Hz), 7.93-7.93 (m, 3H), 7.64 (dd, 1H, $J_1$=7.61 Hz, $J_2$=6.21).

(3) Synthesis of Exemplified Compound 304

The Intermediate Compound 2 obtained according to the reaction formula [2] was used as a starting material, and Exemplified Compound 304 was obtained by a method represented by the following reaction formula [3].

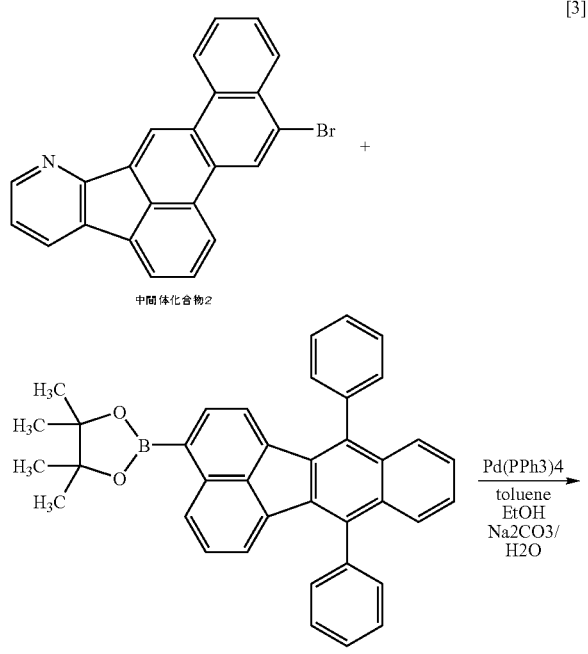

Under a nitrogen atmosphere, 328 mg (0.85 mmol) of the Intermediate Compound 2, 500 mg (0.94 mmol) of 2-(7,12-diphenylbenzo[k]-fluoranthene-3-yl)-4,4,5,5-tetramethyl-1,3,2-dioxaborolane, and 21 mg (0.019 mm) of tetrakis (triphenylphosphine) palladium were suspended in a mixed solvent 40 mL of toluene, 20 mL of ethanol, and 20 mL of 10% aqueous solution of sodium carbonate. The solution was stirred under heat and reflux for 3 hours and then cooled to room temperature to stop the reaction. The organic layer was separated, the organic layer was then washed twice with water. After that, the crystals obtained by addition of methanol were filtrated. The crystals obtained by filtration were purified by silica gel column chromatography (chlorobenzene). The residue obtained by evaporating the solvent under reduced pressure was purified by slurry washing with methanol, and then the crystals obtained by slurry washing were purified twice by recrystallization with chlorobenzene, whereby 225 mg of Exemplified Compound 304 was obtained.

706.0 as M⁺ of the compound was confirmed by MALDI-TOF MS (Matrix Assisted Laser Desorption/Ionization—Time-of-Flight Mass Spectrometry).

$^1$H-NMR (CDCl₃): δ (ppm)=9.71 (s, 1H), 9.12 (d, 1H, J=8.70), 8.71 (s, 1H), 8.69 (d, 1H, J=5.04 Hz), 8.53 (d, 1H, J=8.24 Hz), 8.23 (dd, 1H, $J_1$=8.00 Hz, $J_2$=1.20), 8.0.7 (d, 1H, J=6.87 Hz), 7.82-7.60 (m, 15H), 7.52 (d, 1H, J=7.33 Hz), 7.47-7.43 (m, 2H), 7.37-7.32 (m, 3H), 7.18 (t, 1H, J=7.79 Hz), 6.79 (d, 1H, J=7.33 Hz), 6.64 (d, 1H, J=6.87).

Figure 2:
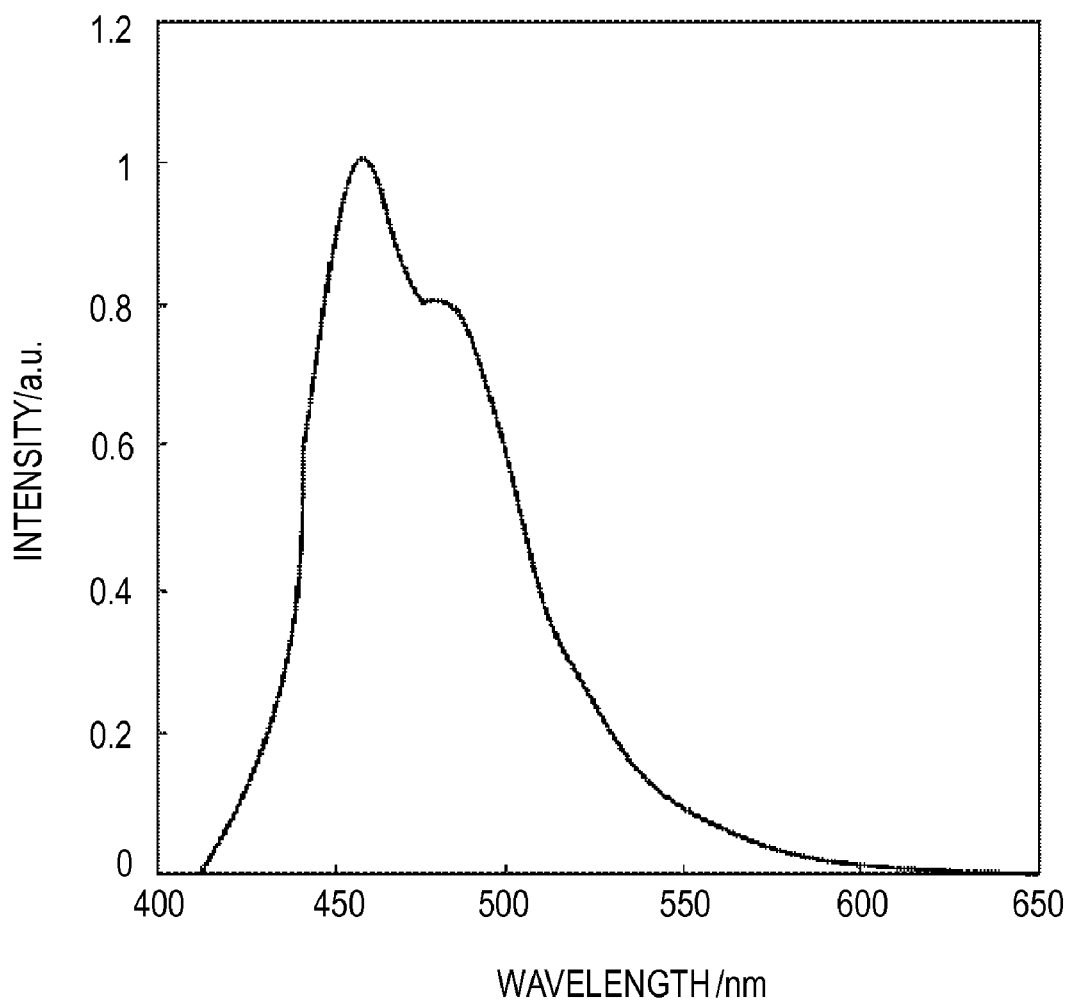
FIG. 2 shows a PL spectrum of a toluene solution ($1.0 \times 10^{-5}$ mol/L) of Exemplified Compound 304.

A PL spectrum of a toluene solution (1.0×10⁻⁵ mol/L) of the Exemplified Compound 304 was measured, and a blue emission spectrum having an emission peak at 458 nm and a half-width of 61 nm was obtained (FIG. 2).

The following Exemplified compounds can be synthesized in the same manner as in Example 1, except that one of the following compounds was used instead of 2-(7,12-diphenylbenzo[k]-fluoranthene-3-yl)-4,4,5,5-tetramethyl-1,3,2-dioxaborolane:

(Exemplified Compound 101): biphenyl-4-yl-boronic acid.
(Exemplified Compound 201): naphthalene-2-yl-boronic acid.
(Exemplified Compound 203): naphthalene-1-yl-boronic acid.
(Exemplified Compound 207): 2-(9,9-dimethyl-9H-fluorene-2-yl)-4,4,5,5-tetramethyl-1,3,2-dioxaborolane.
(Exemplified Compound 228): 4,4,5,5-tetramethyl-2-yl-(9,9,9',9')-tetramethyl-9H-9H'-2,2'-bifluorene-7-yl)-1,3,2-dioxaborolane.
(Exemplified Compound 301): 2-(fluorenthene-3-yl)-4,4,5,5-tetramethyl-1,3,2-dioxaborolane.
(Exemplified Compound 310): 4,4,5,5-tetramethyl-2-(pyrene-1-yl)-1,3,2-dioxaborolane.

(Exemplified Compound 312): 2-(benzo[C]phenanthrene-4-yl)-4,4,5,5-tetramethyl-1,3,2-dioxaborolane.
(Exemplified Compound 314): 2-(indeno[1,2,3-hi]chrysene-6-yl)-4,4,5,5-tetramethyl-1,3,2-dioxaborolane.

The organic light-emitting device with the layer structure explained in the fourth specific example above was produced.

Indium tin oxide (ITO) was formed into a film having a thickness of 120 nm by a sputtering method on a glass substrate so as to serve as the anode, and the resultant was used as a transparent, conductive supporting substrate. The substrate was subjected to ultrasonic cleaning with acetone and isopropyl alcohol (IPA) sequentially. Next, the substrate was washed with pure water and dried. Further, the substrate was subjected to UV/ozone cleaning, and the resultant was used as a transparent, conductive supporting substrate.

A chloroform solution having a concentration of 0.1 wt % was prepared by using Compound A1 represented by the following structural formula as a hole transporting material.

Compound A1

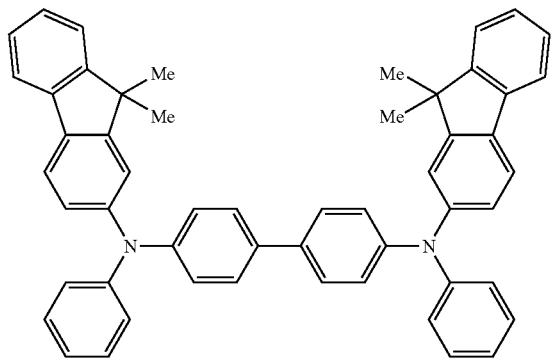

The solution was dropped onto the above ITO electrode, and the whole was subjected to spin coating initially at 500 RPM for 10 seconds and then at 1,000 RPM for 40 seconds, whereby a film was formed. After that, the resultant was dried in a vacuum oven at 80° C. for 10 minutes so that the solvent in the thin film was completely removed. As a result, the hole injection layer was formed. Next, on the hole injection layer, Compound A2 represented by the following formula was deposited into a film in a thickness of 15 nm by a vacuum evaporation method to form a hole-transporting layer.

Compound A2

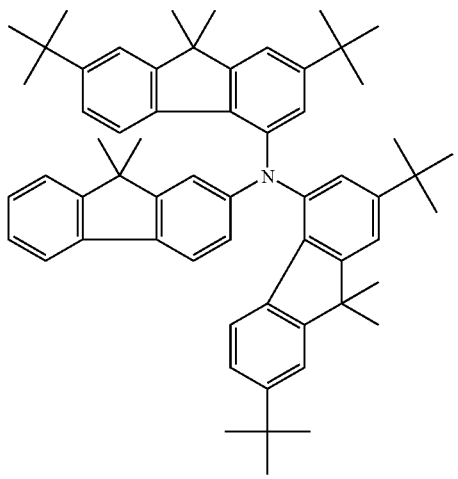

Exemplified Compound 304 shown above and Compound A3 having a structure represented by the following structural formula were co-deposited from the vapor at a weight ratio of 5:95 onto the hole transporting layer, whereby the light emitting layer having a thickness of 30 nm was provided. The layer was formed under conditions including a degree of vacuum at the time of the deposition of $1.0 \times 10^{-4}$ Pa and a deposition rate of 0.1 nm/sec or more to 0.2 nm/sec or less.

Compound A3

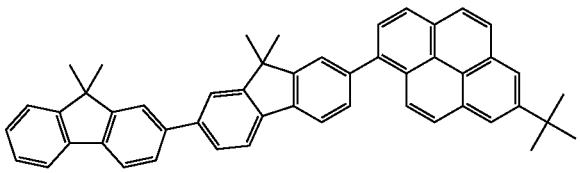

Further, 2,9-bis[2-(9,9'-dimethylfluorenyl)]-1,10-phenanthroline was formed into a film having a thickness of 30 nm by a vacuum vapor deposition method to serve as the electron transporting layer. The layer was formed under conditions including a degree of vacuum at the time of the deposition of $1.0 \times 10^{-4}$ Pa and a deposition rate of 0.1 nm/sec or more to 0.2 nm/sec or less.

Next, lithium fluoride (LiF) was formed into a film having a thickness of 0.5 nm by a vacuum vapor deposition method on the foregoing organic layer. Further, an aluminum film having a thickness of 100 nm was provided by a vacuum vapor deposition method to serve as an electron injecting electrode (cathode), whereby an organic light emitting device was produced. The lithium fluoride film was formed under conditions including a degree of vacuum at the time of the deposition of $1.0 \times 10^{-4}$ Pa and a deposition rate of 0.01 nm/sec. The aluminum film was formed under conditions including a degree of vacuum at the time of the deposition of $1.0 \times 10^{-4}$ Pa and a deposition rate of 0.5 nm/sec or more to 1.0 nm/sec or less.

The resultant organic EL device was covered with a protective plate glass in a dry air atmosphere and sealed with an acrylic resin-based adhesive in order that the device might not deteriorate owing to the adsorption of moisture.

When a voltage of 4.2 was applied to the device thus obtained by using the ITO electrode (anode) as a positive electrode and the Al electrode (cathode) as a negative electrode, blue emission light with an emission efficiency of 8.6 cd/A was observed. Further, the device was observed to emit blue light having CIE chromaticity of x=0.14, y=0.24 was observed.

Further, a voltage was applied to the device for 100 hours under a nitrogen atmosphere with a current density kept at 100 mA/cm². As a result, the initial luminance of 8200 cd/m² reduced to 7350 cd/m² after 100 hours. This means that luminance deterioration was small.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-286726, filed Nov. 7, 2008, which is hereby incorporated by reference herein in its entirety.

What is claimed is:

1. An azaindenochrysene derivative represented by General Formula [1] below:

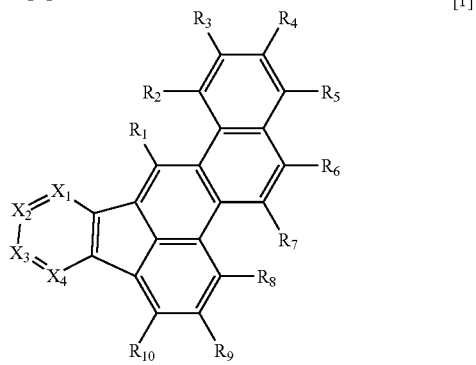

wherein $X_1$ to $X_4$ each represent a carbon atom having a substituent R or a nitrogen atom, the carbon atom or the nitrogen atom forming a ring;

R represents a hydrogen atom or a group selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group, provided that at least one of $X_1$ to $X_4$ represents a nitrogen atom, and in a case where a plurality of carbon atoms having a substituent R are present, each R is independently identical to or different from each other; and $R_1$ to $R_{10}$ each represent a hydrogen atom, a halogen atom, or a group selected from at least one of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group, provided that $R_1$ to $R_{10}$ are independently identical to or different from each other.

2. The azaindenochrysene derivative according to claim 1, wherein $R_6$ is selected from at least one of a halogen atom, a substituted or unsubstituted aryl group, a substituted or unsubstituted fused polycyclic aromatic group, and a substituted or unsubstituted fused polycyclic heterocyclic group.

3. The azaindenochrysene derivative according to claim 1, wherein $X_1$ and $X_4$ are nitrogen atoms.

4. The azaindenochrysene derivative represented by General Formula [2] below:

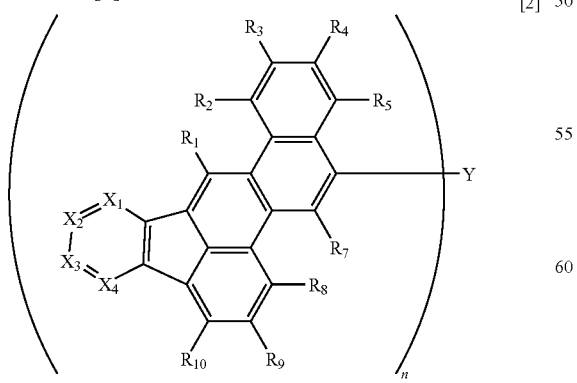

wherein $X_1$ to $X_4$ each represent a carbon atom having a substituent R or a nitrogen atom, the carbon atom or the nitrogen atom forming a ring;

R represents a hydrogen atom or a group selected from at least one of a substituted or unsubstituted alkyl group, a substituted or unsubstituted aryl group, a substituted or unsubstituted heterocyclic group, a substituted or unsubstituted fused polycyclic aromatic group, and a substituted or unsubstituted fused polycyclic heterocyclic group, provided that at least one of $X_1$ to $X_4$ represents a nitrogen atom, and in a case where a plurality of carbon atoms having a substituent R are present, each R is independently identical to or different from each other;

$R_1$ to $R_5$ and $R_7$ to $R_{10}$ each represent a hydrogen atom, a halogen atom, or a group selected from at least one of a substituted or unsubstituted alkyl group, a substituted or unsubstituted alkenyl group, a substituted or unsubstituted alkynyl group, a substituted or unsubstituted aryl group, a substituted or unsubstituted heterocyclic group, a substituted or unsubstituted fused polycyclic aromatic group, and a substituted or unsubstituted fused polycyclic heterocyclic group;

$R_1$ to $R_5$ and $R_7$ to $R_{10}$ are independently identical to or different from each other; and Y represents at least one of a single bond and an n-valent linking group derived from at least one of a substituted or unsubstituted alkane, a substituted or unsubstituted alkene, a substituted or unsubstituted alkyne, a substituted or unsubstituted aromatic compound, a substituted or unsubstituted heterocyclic compound, a substituted or unsubstituted fused polycyclic aromatic compound, and a substituted or unsubstituted fused polycyclic heterocyclic compound, provided that n is an integer of equal to or greater than 2 and equal to or less than 4.

5. The azaindenochrysene derivative according to claim 4, wherein $X_1$ and $X_4$ are nitrogen atoms.

6. An organic light-emitting device having an anode, a cathode, and an organic compound layer interposed between the anode and the cathode, wherein the organic compound layer comprises at least one compound according to claim 1.

7. The organic light-emitting device according to claim 6, wherein the organic compound layer is a light-emitting layer comprising at least a host and a guest, and the compound represented by the General Formula [1] is either the host or the guest.

8. An organic light-emitting device having an anode, a cathode, and an organic compound layer interposed between the anode and the cathode, wherein the organic compound layer comprises at least one compound according to claim 4.

9. The organic light-emitting device according to claim 8, wherein the organic compound layer is a light-emitting layer comprising at least a host and a guest, and the compound represented by the General Formula [2] is either the host or the guest.

* * * * *